US008222293B2

(12) United States Patent
Silva et al.

(10) Patent No.: US 8,222,293 B2
(45) Date of Patent: Jul. 17, 2012

(54) TREATING LEARNING DEFICITS WITH INHIBITORS OF HMG COA REDUCTASE

(75) Inventors: Alcino Silva, Sherman Oaks, CA (US); Yijun Cui, Los Angeles, CA (US); Weldong Li, Shanghai (CN); Steven A. Kushner, Rotterdam (NL)

(73) Assignee: Regents of the University of Carolina, Oakland, CA (US)

( * ) Notice: Subject to any disclaimer, the term of this patent is extended or adjusted under 35 U.S.C. 154(b) by 1485 days.

(21) Appl. No.: 11/569,426

(22) PCT Filed: May 23, 2005

(86) PCT No.: PCT/US2005/018129
§ 371 (c)(1), (2), (4) Date: Nov. 20, 2006

(87) PCT Pub. No.: WO2005/120496
PCT Pub. Date: Dec. 22, 2005

(65) Prior Publication Data
US 2007/0299096 A1 Dec. 27, 2007

Related U.S. Application Data

(60) Provisional application No. 60/574,442, filed on May 24, 2004, provisional application No. 60/661,764, filed on Mar. 14, 2005.

(51) Int. Cl.
*A61K 31/35* (2006.01)
*A61K 31/47* (2006.01)

(52) U.S. Cl. ........................................ 514/460; 514/307
(58) Field of Classification Search ................. 514/460, 514/307
See application file for complete search history.

(56) References Cited

U.S. PATENT DOCUMENTS
6,310,212 B1 * 10/2001 Yuan et al. ................... 546/153

FOREIGN PATENT DOCUMENTS
| WO | WO 95/06470 | * | 3/1995 |
| WO | WO 00/16778 | * | 3/2000 |
| WO | WO 01/32161 | * | 5/2001 |
| WO | WO 01/45698 | * | 6/2001 |

OTHER PUBLICATIONS

Huang et al. "(+)-hydrastine, a potent competitive antagonist at mammalian GABAA receptors," Br. J. Pharmacol., 1990, vol. 99, pp. 727-730.*
Gutmann et al. "Mouse Models of Neurofibromatosis 1 and 2" Neoplasia, 2002, vol. 4, No. 4, pp. 279-290.*

* cited by examiner

*Primary Examiner* — Shengjun Wang
(74) *Attorney, Agent, or Firm* — Suzannah K. Sundby, Esq.; Smith, Gambrell & Russell, LLP

(57) ABSTRACT

The disclosure provides methods of treating cognitive disorders by administering a HMG CoA reductase inhibitor. Cognitive deficits treatable with the inhibitor compound include those associated with Angelman Syndrome, Neurofibromatosis-1, certain forms of X-linked mental retardation, tuberous sclerosis, Down Syndrome, autism, and attention deficit/hyperactivity disorder.

22 Claims, 4 Drawing Sheets

TREATING LEARNING DEFICITS WITH INHIBITORS OF HMG COA REDUCTASE

1. STATEMENT REGARDING FEDERALLY SPONSORED RESEARCH

Figure 1:
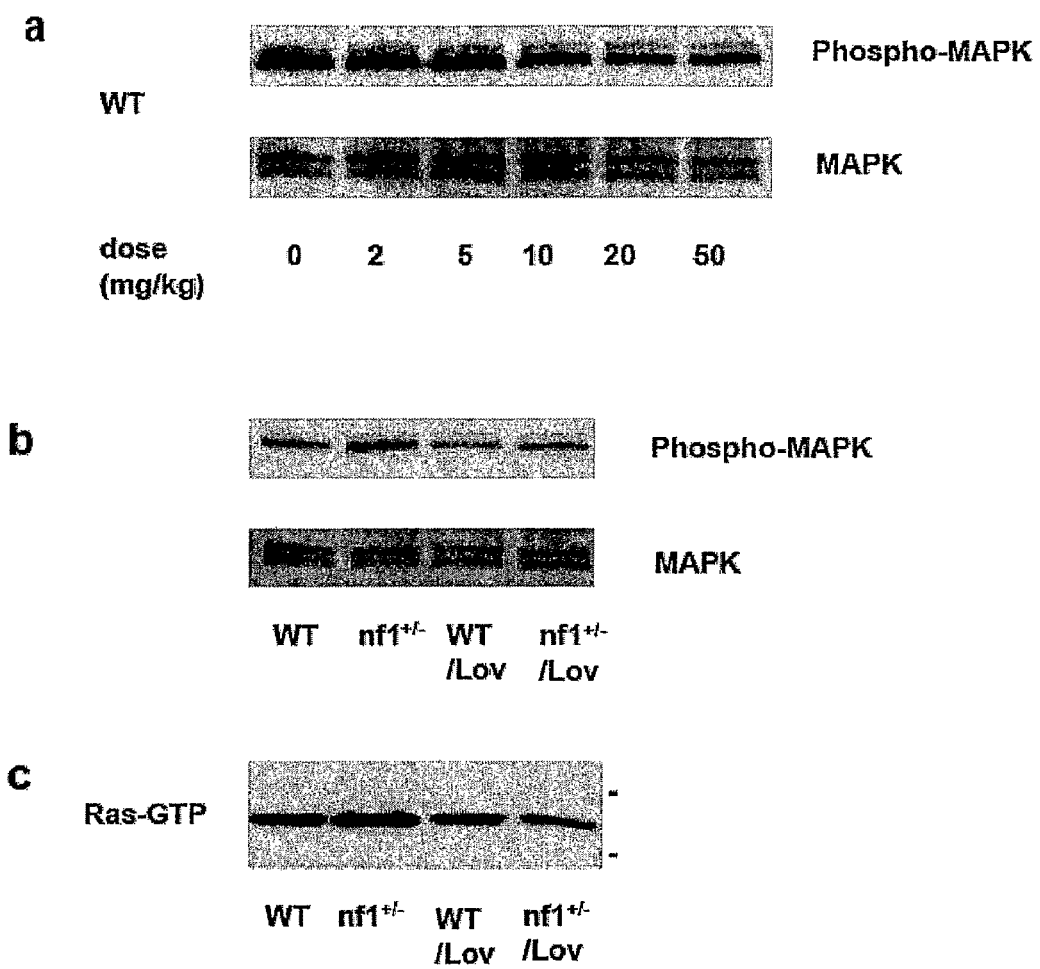

This invention was made with Government support under Grant Nos. NS038480 and AG013622, awarded by the National Institutes of Health, and Grant No. DAMD17-02-1-0637, awarded by the U.S. Army. The Government has certain rights in this invention.

2. TECHNICAL FIELD

The disclosure provides methods and compounds for treating learning and memory deficits and other cognitive disorders.

3. INTRODUCTION

Cognition is a complex neurological process where stimuli are received and processed by the neuronal circuitry into perception and memory, and where such processed information becomes transformed into reasoning, judgment, awareness, and creativity. Some understanding of the biological basis for the complex cellular mechanisms that underlie cognition have come from identification of genes affecting cognitive abilities in various animal models and the molecular analysis of genetic abnormalities in the human population that lead to impairment of various cognitive processes.

The genetic defects identified as affecting cognitive function implicate a diverse array of molecular mechanisms. A number of genes are involved in signaling pathways, including serine-threonine kinase RSK2 implicated in Coffin-Lowry syndrome, neurofibromin implicated in Neurofibromatosis-1 (NF-1), and signaling by small monomeric guanine nucleotide (GTP) binding proteins implicated in a number of mental retardation (MR) syndromes. Protein degradation pathways may also be involved, as indicated by the identification of UBE3A gene affected in Angelman syndrome. Transcription factors and transcriptional regulation in cognitive processes are implicated by defects of CREB Binding Protein (CBP) in Rubinstein-Taybi syndrome, mutations in transcription repressor methyl-CpG binding protein in Rett syndrome, and defects in helicase/histone deacetylase XH2 protein in α-thalassemia (ATR-X syndrome). Protein synthesis appears affected by mutations in the FMR1 gene associated with fragile X mental retardation.

Although the identified genes affecting cognitive function have diverse activities, it is suggested that they are related by their effect on the signaling pathways involved in memory formation, synaptic development, and synaptic maturation. For instance, Ras mediated signal transduction may affect the mitogen-activate protein kinase (MAPK) signaling pathway involving MEK and ERK, which are part of a pathway involved in regulating the activity of transcription factor CREB involved in consolidation of memory and learning. Genes regulated by CREB are believed to affect long term changes in synaptic properties, such as responsiveness to neurotransmitters, membrane excitability, and number and size of synapses. Additional lines of evidence linking such pathways with cognitive function are provided by the effect of the kinase activity of RSK2 in Coffin Lowry syndrome and the CBP in Rubinstein-Taybi syndrome in modulating the activity of transcription factor CREB.

Although the underlying cause of other cognitive disorders, such as autism and attention deficit/hyperactivity disorder (ADHD) have not been identified, there are indications that the dysfunction in these conditions may also arise, at least in part, in the cellular pathways involved in regulating synaptic activity and functional plasticity. For example, some Rett syndrome patients display autistic symptoms, while subjects diagnosed with autism have abnormal expression of the gene associated with Rett syndrome (Samaco, R. C. et al., *Hum Mol Genet.* 13(6):629-39 (2004)). Furthermore, characteristics of ADHD, which is a heterogeneous set of dysfunctions characterized by deficits in sustained attention, behavioral over activity, and impulsivity, are also observed in some molecularly characterized cognitive disorders such as NF-1 (Barton, B. and North, K., *Dev. Med. Child Neurol.* 46(8): 553-63 (2004)).

Although an understanding of the molecular basis of cognitive function has advanced significantly, treatments for the cognitive deficits associated with disorders of known and unknown etiology have focused primarily on use of cognitive or physical therapy to treat the symptoms of the disorder. These include regimens emphasizing psychomotor development, speech therapy, and special educational programs. Drug treatments, where available, typically involve compounds affecting neurotransmitter activity. For example, one treatment of Rett syndrome patients uses L-Dopa to improve rigidity. Modulating glutamate receptor activity is the target of dextromethorphan treatment in Rett syndrome and also the focus of treatments with benzamide derivatives for fragile X syndrome (see Danysz, W., *Curr. Opin. Investig. Drugs.* 3(7): 1081-8 (2002)). ADHD has traditionally been treated with phychotropic drugs, such as methylphenidate and pemoline. Although they may ameliorate behavioral problems associated with hyperactivity, improvements in cognitive function may not be significant.

Although drug therapies targeting neurotransmitters and their receptors have a place in the treatment of cognitive disorders, there is a need in the art for therapies targeting the molecules and cellular pathways involved in cognitive function. Modulating the underlying molecular basis responsible for a cognitive deficit may provide longer lasting improvements in cognitive function in subjects afflicted with these disorders.

4. SUMMARY

The present disclosure provides methods of treating cognitive disorders by administering an effective amount of a hydroxymethylglutaryl CoA (HMG CoA) reductase inhibitor, where the subject has a level of cholesterol that does not warrant therapeutic intervention with the inhibitor to lower the cholesterol levels. Generally, the class of HMG CoA reductase inhibitor compounds useful in the treatments are statins, which are normally prescribed to treat hypercholesterolemia. Dosages of the inhibitor administered may be the dosages generally used to lower serum cholesterol levels in subjects afflicted with hypercholesterolemia. In some embodiments, dosages of the inhibitors may comprise amounts that do not effectively lower cholesterol levels in hypercholesterolemic patients but which are effective in treating the cognitive disorder. In some embodiments, the HMG CoA reductase inhibitors may be used in combination with other inhibitor compounds, including farnesyl transferase inhibitors, geranygeranyltransferase inhibitors, and inhibitors of inhibitory neuronal activity (e.g., antagonists and inverse agonists of GABA receptors)

Various disorders that manifest cognitive disorders may be treated with the HMG CoA reductase inhibitors. These include cognitive deficits associated with genetic abnormalities such as Angelman Syndrome, Down Syndrome, neurofibromatosis NF-1, X-linked mental retardation gene OPHN1, and tuberous sclerosis. In other embodiments, identifiable cognitive disorders of unknown etiology but which share disease characteristics with cognitive disorders of a known genetic basis may be treated. Exemplary disorders of this type are attention deficit/hyperactivity disorder (ADHD) and autism.

In other embodiments, the inhibitor compounds are used to treat cognitive disorders associated with dysregulation of the basic cellular processes believed to be responsible for cognitive function. These include dysregulation of small monomeric GTP binding proteins implicated in learning and memory, such as Ras, Rho, Rab, Sar1/Arf and Ran and their associated signaling pathways. In other embodiments, the cognitive disorders treatable with the compounds are associated with dysfunction in MAPK pathways and/or inhibitory neuronal activity.

In some embodiments, the inhibitor compounds are used to modulate the cellular correlates of cognitive function, such as early and late forms of LTP. Because HMG CoA reductase inhibitors appear to have no measurable effect on subjects with normal cognitive function, the inhibitors are indicated for systems displaying an abnormal LTP. Thus, in some embodiments, a neural system with a depressed LTP response is contacted with an effective amount of the inhibitor to modulate the LTP response.

Further provided herein are various compositions of inhibitor compounds, including combinations of a HMG CoA reductase inhibitor and a farneysl transferase inhibitor, HMG CoA reductase inhibitor and a geranylgeranyl transferase inhibitor, and HMG CoA reductase inhibitor and an inhibitor of GABA receptor activity. In some embodiments, the compositions comprise a HMG CoA reductase inhibitor and an excipient, where the HMG CoA reductase inhibitor is present in an amount that does not significantly lower serum cholesterol level but which is effective in treating a cognitive disorder.

5. BRIEF DESCRIPTION OF THE FIGURES

FIG. 1 shows down-regulation of p21Ras-MAPK activity in $nf1^{+/-}$ mice by Lovastatin. a, Lovastatin decreased active MAPK (phosphor-p44/42) in WT mice in a dose-dependent manner; b, Lovastatin was effective at decreasing active MAPK in the $nf1^{+/-}$ mice; c, Lovastatin also decreased active p21Ras (p21Ras-GTP) in $nf1^{+/-}$ mice.

Figure 2:
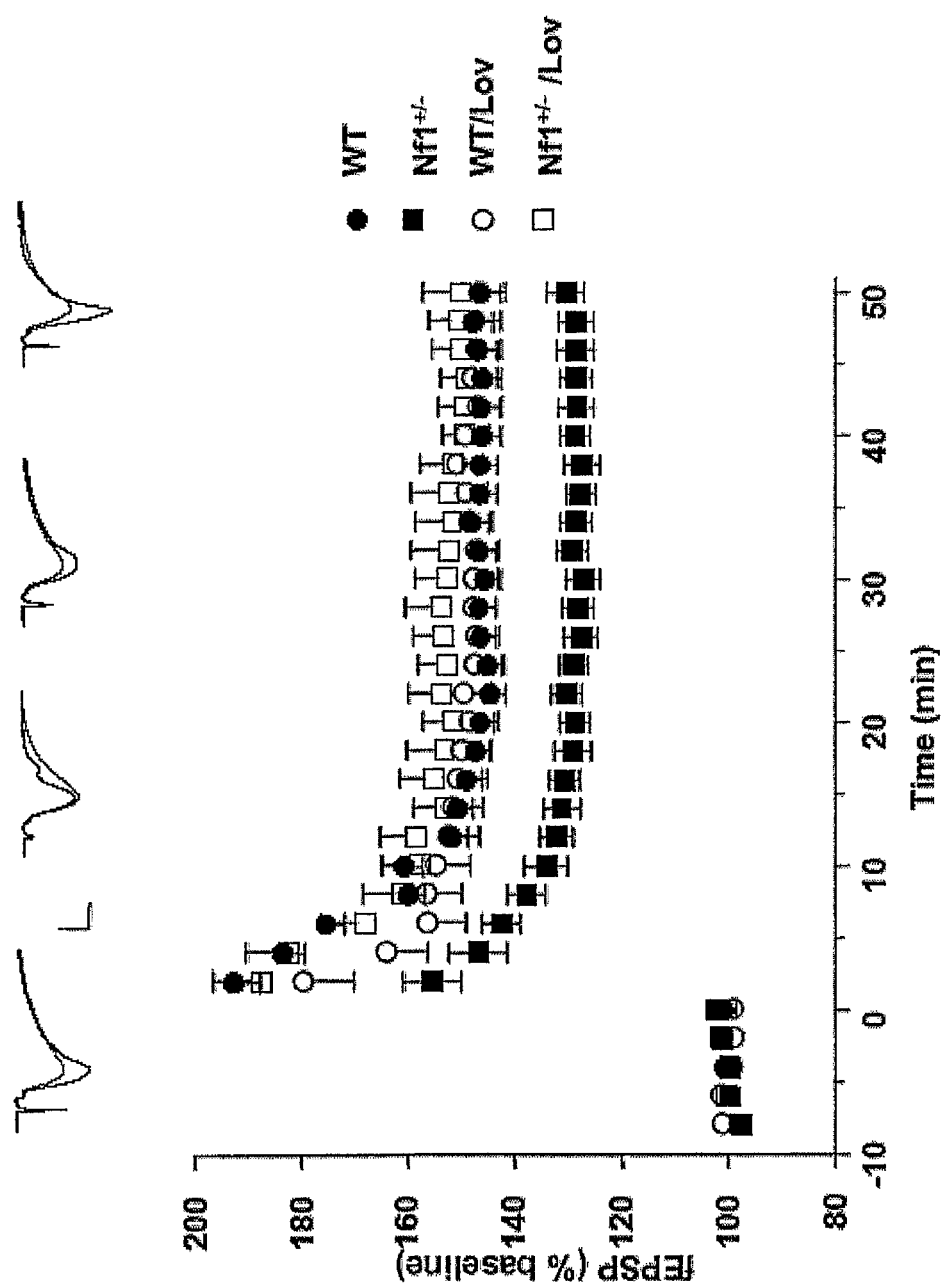

FIG. 2 shows rescue by lovastatin of $Nf1^{+/-}$ deficits in long-term potentiation. Percentage of baseline field EPSP (fEPSP) is plotted over time. A five theta-burst induction protocol was delivered at time 0 (WT=8, $nf1^{+/-}$=7, WT with lovastatin=8, $nf1^{+/-}$ with lovastatin=7). For clarity purposes, error bars (standard error of the mean) are shown in only one direction. Representative traces are shown from left to right: WT off drug, $nf1^{+/-}$ off drug, WT on lovastatin, $nf1^{+/-}$ on lovastatin. Horizontal bar represents 2 ms. Vertical bar represents 0.5 mV.

Figure 3:
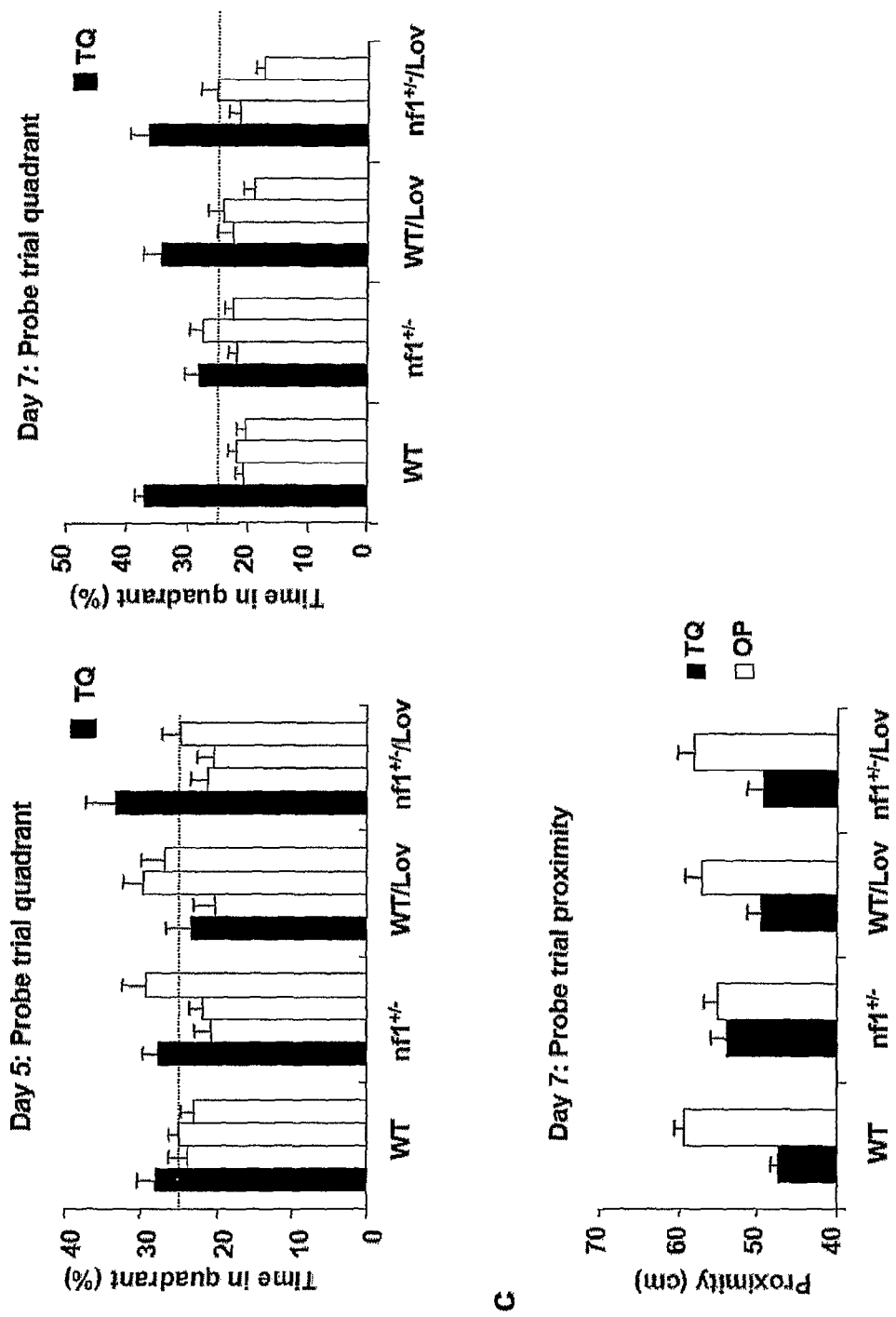

FIG. 3 shows lovastatin rescue of spatial learning deficits in $nf1^{+/-}$ mice. a, Percent time spent in each quadrant during a water maze probe trial on day 5; b, Percent time spent in each quadrant during a probe trial on day 7; c, Average proximity to the exact position where the platform was during training, compared with proximity to the opposite position in the water maze. Quadrants are training quadrant (TQ), adjacent left, opposite quadrant (OP) and adjacent right. (WT=24, $nf1^{+/-}$=21, WT with lovastatin=21, $nf1^{+/-}$ with lovastatin=20)

Figure 4:
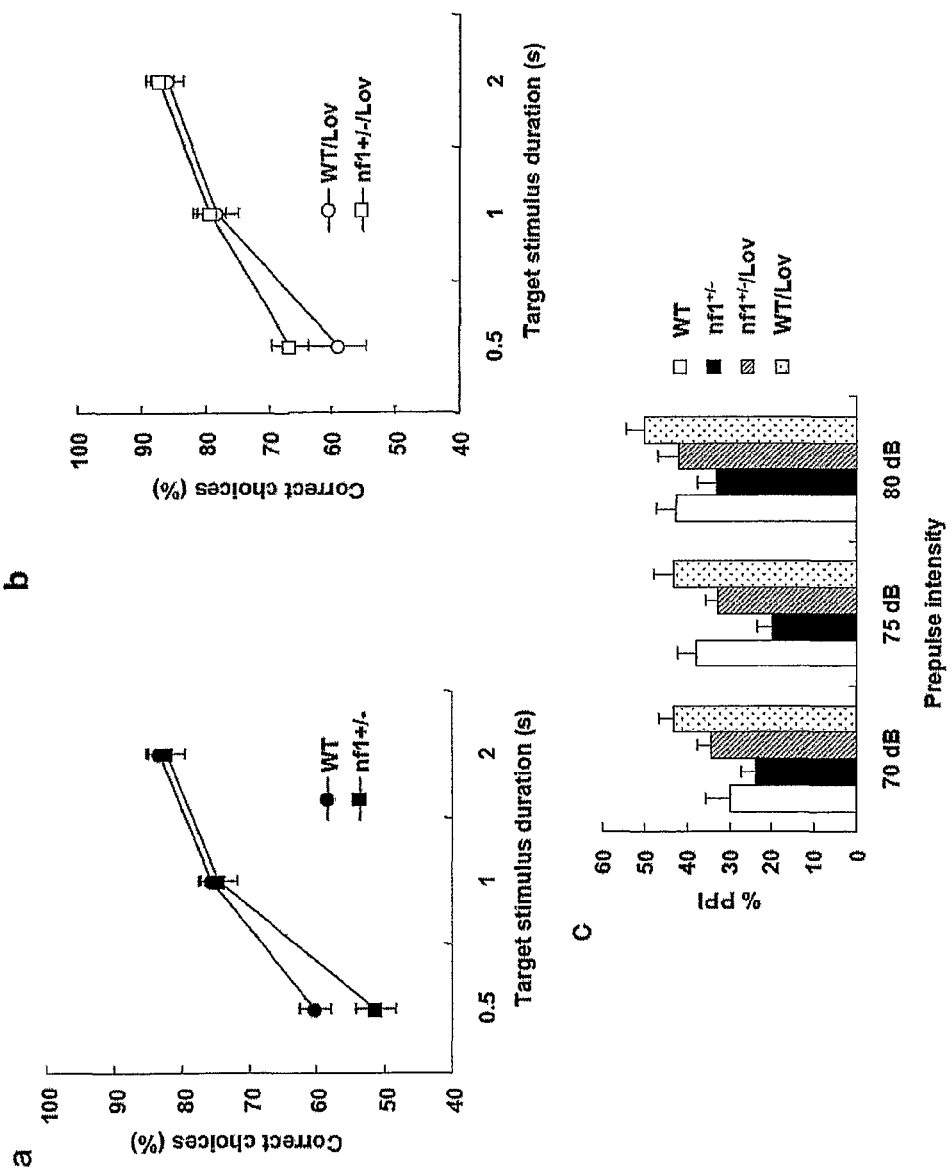

FIG. 4 shows attention deficit in $nf1^{+/-}$ mice and reversal of the attention and sensory gating deficit by treatment with lovastatin. a, Tests in the lateralized reaction task in which target-stimulus durations are randomly varied within session. Target durations are 0.5, 1.0, or 2.0 sec. Correct choice rate is plotted for WT and $nf1^{+/-}$ mice off lovastatin (WT=10, $nf1^{+/-}$=14); b, Correct choice rate is plotted for WT and $nf1^{+/-}$ mice on lovastatin (WT with lovastatin=7, $nf1^{+/-}$ with lovastatin=7); c, PPI was examined using prepulses at three different stimulus intensities (70, 75 and 80 dB) (WT=8, $nf1^{+/-}$=8, WT with lovastatin=9, $nf1^{+/-}$ with lovastatin=9).

6. DETAILED DESCRIPTION OF EMBODIMENTS

The present disclosure provides methods of treating cognitive deficits by use of inhibitors of hydroxymethylglutaryl CoA (HMG CoA) reductase. Cognitive deficits that may be treated by the methods herein include those associated with known genetic abnormalities and cognitive deficits displaying clinical symptoms similar to, and in many cases overlapping with the identified genetic causes of the cognitive dysfunction.

The compounds and compositions for use in the methods herein comprise inhibitors of the enzyme HMG-CoA reductase, which catalyzes the conversion of HMG-CoA to mevalonate, the isoprenoid intermediate used for cholesterol biosynthesis. An important class of HMG CoA inhibitor compounds is statins, which are used to treat subjects with hypercholesterolemia to decrease serum cholesterol and reduce the risk of associated diseases, such as heart disease and atherosclerosis. Although the beneficial effects of statins reside in their ability to lower cholesterol, the effects of the drug are pleiotropic. Statins appear to affect endothelial cell function via its effect on NO production and inhibition of reactive oxygen species, proliferation of smooth muscle cells, inhibition of platelet function, and suppression of vascular inflammation. In some instances, statin therapy is linked to peripheral neuropathies characterized by degeneration of nerves in a progressive and graded fashion. Sensory nerves, for instance those sensing heat or pain, appear most sensitive, but motor nerves and nerves involved in coordination of movement are also involved. Thus, the art suggests that statins may not be indicated for disorders affecting the nervous system. The pleiotropic effects of statin are thought to be associated with its interference with the attachment of lipid moieties to various regulatory proteins.

Although statins are generally administered for treating hypercholesterolemia, it is shown here that subjects suffering from cognitive deficits associated with specific disorders, but who do not display abnormal cholesterol levels, may benefit in improved cognitive function that is adversely affected in the particular disorder. Dose of statins comparable to the dosage generally prescribed for hypercholesterolemia is shown to have beneficial effects, and subjects with normal cognitive function are not affected upon treatment with statins, suggesting that the statins are affecting a physiological process that is abnormal or imbalanced in the afflicted subject. Moreover, the studies herein show that statins may cross the blood-brain barrier and have therapeutic effect on neuronal cells to improve cognitive function in subjects whose blood brain barrier may not be compromised by traumatic injury, or age related diseases such as Alzheimer's or other dementias.

6.1 Treatment of Cognitive Deficits

In accordance with the above, the methods disclosed herein comprise administration of a HMG-CoA reductase inhibitor to improve, enhance, or restore the cognitive function of subjects suffering from a cognitive deficit. "Cognitive function" as used herein refers to the performance of some cognitive activity, such as memory, perception, learning, and reasoning. "Learning" refers to acquisition of information and/or knowledge, and is typically evaluated by exposing a subject to a learning experience and observing changes in behavior arising from that experience. Learning may be categorized as non-associative and associative. Non-associative learning occurs when a subject is exposed to a single stimulus in the absence of any other connected stimulus. Habituation and sensitization are two examples of non-associative learning. Associative learning occurs when a subject is exposed to a stimulus in association with another stimulus or where a stimulus is associated with the organism's behavior. Examples of associative learning are classical conditioning or operant conditioning.

"Memory" refers to the storage and retrieval of information. Memory is generally classified into short term memory (also called working memory) and long term memory, where consolidation into long term memory is believed occur through a stage involving short term memory. Short-term memory lasts for period of seconds to minutes, up to several days but which is subject to disruption and loss. Long-term memory is durable and can last for years, up to the life of the subject. As further described below, a correlate of learning and memory at the cellular level is long term potentiation (LTP), which is an increase in synaptic strength (i.e., potentiation) that occurs following a train of stimuli of an afferent neural pathway. There are different components to LTP that mimic short term and long term memory. Short-term component of LTP typically follows a single train of stimuli, is durable for minutes, and is not blocked by inhibitors of protein synthesis. Long-term component of LTP (L-LTP) can be induced by multiple trains of stimuli, may last for hours to weeks, and requires transcription and protein synthesis. Modulation of LTP is associated with activation of glutamate receptors as well as activity of inhibitory GABA receptors (Remondes, M. et al., *Learn Mem.* 10(4):247-52 (2003)).

Correspondingly, "cognitive disorder" refers to a disorder that affects mental processes, including impairments of memory, learning, awareness, attention, communication, motor coordination, and/or intellectual capacity. "Impairment of cognition," or "cognitive deficits" as used herein, are associated with various disorders, including among others, developmental disabilities, such as mental retardation, autism, dyslexia, attention deficit/hyperactivity disorder, ischemic stroke, traumatic brain injury, Alzheimer's Disease, degenerative dementia, obsessive compulsive disorder, and schizophrenia. Such disorders are often accompanied by personality and behavioral differences. However, a cognitive deficit as used herein specifically excludes impaired cognitive abilities associated with age related disorders, such as Alzheimer's and degenerative dementias. An "age related disorder" refers to a disorder in which the subject exhibits normal cognitive abilities and function for an extended time period from birth, but where cognitive function declines with passage of time. For instance Alzheimer's is considered an age related disease where the affected subject has normal cognitive abilities for much of the individual's life until onset of the disease in late stages of life. Although genetic abnormalities may contribute to a familial form of Alzheimer's disease characterized by early onset, the time period for manifestation of cognitive decline still requires about 30-50 years.

Humans with intellectual disabilities are those who develop at a below average rate and experience difficulty in learning and social adjustment. Intellectual disabilities refers to significantly subaverage general intellectual functioning existing concurrently with deficits in adaptive behavior and manifested during the developmental period that adversely affects a subject's educational performance. General intellectual functioning is typically measured by an intelligence test that is adjusted for the developmental level to which the test subject is a member.

"Subject" as used herein refers to an animal or a patient for whom is intended the described treatment. Subjects include, aves (e.g., chickens, pigeons, owls), and mammals, including by way of example and not limitation, members of rodentia (e.g., mouse, rat, guinea pig), lagomorpha (e.g., rabbits, hares), perissodactyla (e.g., horses, donkeys, etc.), artodactyla (e.g., pigs, cows, sheep), carnivora (e.g., cats, canines), and primates (e.g., apes, monkeys, baboons, and humans). Subjects also include animals modified using recombinant DNA and/or transgenic techniques, such as animals modified to inactivate, overexpress, or misexpress genes involved or suspected of involvement in cognitive function.

In some embodiments, subject as used herein specifically excludes those within a population for whom HMG CoA reductase inhibitors are medically prescribed for higher than normal cholesterol levels, or for elevated cholesterol levels that result in adverse effects on cognitive function. A normal level of cholesterol is a level that generally does not warrant therapeutic use of HMG CoA reductase inhibitors and/or a level that does not manifest itself in a cognitive deficit in a specified class of subjects or in the general population. This level will depend on the subject and variations in cholesterol levels observed with respect to age, sex, and the population type. Generally, cholesterol levels are measured when the subject is not suffering from an acute illness, not under stress, and for a woman, when not pregnant. The level of cholesterol as used herein refers to the total serum cholesterol level, which includes the combined cholesterol found in sera in the form of high density lipoprotein (HDL), intermediate density lipoprotein (IDL), low density lipoprotein (LDL) and very low density lipoprotein (VLDL).

An exemplary normal cholesterol level for a human is that below about the 95th percentile of the general population pool, below about the 85th percentile of the general population pool, below about the 75th percentile of the general population pool, below about the 50th percentile of the general population pool to about the 25th percentile of the general population pool. Thus, in some embodiments, a normal level for a human is below about 240 mg/dL, below about 220 mg/dL, below about 200 mg/dL, below about 190 mg/dL, below about 180 mg/dL, or below about 170 mg/dL, where the lower limit of cholesterol level is that considered healthy for the subject, such as about 120 mg/dL, 140 mg/dL, or 150 mg/dL, depending on various factors, such as the age and sex of the subject. A level consider healthy for a child or adolescent is between about 120 mg/dL and about 170 mg/dL. An exemplary normal level of serum cholesterol for a human adult is a range that is below about 240 mg/dL or below about 200 mg/dL to about 140 mg/dL. Thus, in some embodiments, the population of subjects treatable using the methods herein include children, adolescents, and adults who do not have abnormally elevated cholesterol levels and who have not manifested age related cognitive disorders, as described above.

In some embodiments, the cholesterol level may be based on the amount of cholesterol in the LDL fraction. Cholesterol and triglycerides found in sera fractionate into various components: HDL, IDL, LDL, and VLDL. The LDL fraction derives from VLDL, and elevated levels of total serum cholesterol and cholesterol in the LDL (c-LDL) fraction are correlated with increased risk of atherosclerosis. In some embodiments, the normal level of c-LDL for a human is that below about the 95th percentile of the general population pool, below about the 85th percentile of the general population pool, below about the 75th percentile of the general population pool, below about the 50th percentile of the general population pool, to about the 25th percentile of the general population pool. Thus, in some embodiments, the c-LDL level is less than about 160 mg/dL, less than about 130 mg/dL, or less than about 100 mg/dL with the lower limit being a level of c-LDL that is considered a healthy level.

In addition to subjects with above-normal levels of serum cholesterol who are prescribed HMG CoA reductase inhibitors, another class of subjects for whom the treatment is not intended is those with certain defects in cholesterol biosynthesis. Defects in synthesis of intermediates prior to formation of squalene are not indicated for treatment with statins. For instance, there is a single human genetic disorder arising from a deficiency of mevalonate kinase known to affect this portion of the cholesterol biosynthetic pathway. Subjects with defects in the cholesterol biosynthetic pathway downstream of the squalene intermediate are also generally excluded, although it is to be understood that the cognitive deficits arising from such disorders, such as Smith-Lemli-Opitz syndrome, might benefit from treatment from statins.

A variety of cognitive disorders may be treated using the inhibitor compounds described herein. In some embodiments, the cognitive disorder is associated with a known genetic abnormality. Generally, the types of genetic defects for which the attendant cognitive disorders are amenable to treatment with the inhibitors herein are typically those associated with dysregulation of mitogen activated protein kinase (MAPK) signaling pathway, dysregulation of signaling pathways involving small monomeric GTP binding proteins, and/or dysregulation of inhibitory neuronal activity. As used herein, "dysregulation" or "dysfunction" refers to impaired or abnormal function of the specified process, including, loss of normal function, or their overactivation or underactivation. In the context of genetic abnormalities, dysregulation of a cellular process may arise from a genetic change that causes a loss of function, increased dosage, or altered activity of the molecules involved, directly or indirectly, in the cellular process.

Generally, genetic defects may be categorized based on the type of genetic alteration. Segmental aneusomy results from the deletion or duplication of a specific chromosomal region such that there is an inappropriate dosage of critical gene(s). The gene dosage may result from increased or decreased expression at a single gene (i.e., single locus) or from multiple genes (i.e., multi-locus). Examples of segmental aneusomy that display cognitive disorders treatable with the compounds described herein, include, among others, Angelman syndrome and Down Syndrome.

Angelman Syndrome (AS) is associated with the deletion of chromosomal region 15q11-q13, and although the deletion overlaps with chromosomal deletions resulting in another form of mental retardation syndrome termed Prader Willi syndrome (PWS), AS occurs when the deletion is on a maternally inherited chromosome while PWS occurs when the deletion is on a paternally inherited chromosome. Different classes of AS are known based on the location of the cytogenetic abnormality. Molecular analysis indicates that the affected gene in one form of AS encodes an ubiquitin ligase, UBE3A, a protein involved in the ubiquitin mediated protein degradation pathway (Kishino, T. et al., $Nature\ Genetics$ 15:74-77 (1997)). In the normal brain, the copy of UBE3A inherited from the father is almost completely inactive through genetic imprinting such that the maternal copy performs most of the UBE3A function in the brain. Because of this imprinting phenomena, AS phenotype is typically seen when the maternal copy is affected. Another form of AS is characterized by biparental inheritance of imprinted gene in the deleted region with a paternal only methylation pattern. The deleted region termed IC is hypothesized to act by resetting the male-female genomic imprint during oogenesis and the female-male imprint during spermatogenesis. In other words, the IC acts as a switch that turns on the maternal copy of UBE3A while silencing the paternal copy of the gene. Mutations and deletions in this critical region prevent the maternal to paternal imprinting switch in the AS families. Individuals with mutations in IC inherit the paternal imprint pattern on the mutant chromosome resulting in the inability to turn on the maternal UBE3A gene. Another form of AS is paternal uniparental disomy (UPD), where the child inherits both copies of chromosome 15 from the father, with no copy inherited from the mother. In this case, there is no deletion or mutation, but the child is still missing the active UBE3A gene because the paternal-derived chromosomes only have brain-inactivated UBE3A genes. Mouse models of AS have been created by knockout of the corresponding mouse UBE3A gene. These animals show impairment of LTP, abnormal levels of p53 activity due to the reduction in its degradation by the ubiquitin pathway, and a dysregulation of CaMKII activity (Jiang, Y. H. et al., $Neuron$ 21(4):799-811 (1998); Weeber, E. J. et al., $J.\ Neurosci.$ 23(7):2634 (2003)). Studies suggest an association between CaMKII activity and activation of Ras GTPase activating protein (Song B. et al., $Brain\ Res.$ 1005(1-2):44-50 (2004); Oh, J. S. et al., $J\ Biol\ Chem.$ 279(17):17980-8 (2004)). In addition, some of the deletions in Angelman syndrome also removes the β3 subunit of the GABA receptor, suggestive of dysregulation of GABA receptor activity for some of the cognitive disorders associated with AS. Interestingly, autism is also correlated with polymorphisms of the β3 subunit of the GABA receptor.

In other embodiments, the compounds and compositions are used to treat the learning disorders associated with trisomy of chromosome 21, more commonly known as Down Syndrome (DS), which is a segmental aneusomy believed to affect expression of multiple genes. DS is the most common and readily identifiable chromosomal condition associated with mental retardation and is most often caused by an abnormality during cell division in gamete formation called nondysfunction. The extra copy of chromosome 21 appears to interfere with normal growth and development. The cause of the mental retardation in DS has not been identified, although the over-expression of genes located on the trisomic region is assumed to be responsible for the phenotypic abnormalities of DS. However, in a mouse model of DS characterized by trisomy for chromosome 16, there is severe abnormality in the induction of LTP that may result from over activation of inhibitory pathways that reduce neuronal activation by metabotropic glutamate receptors (Kleschevnikov, A. M. et al., $J\ Neurosci.$ 24(37):8153-8160 (2004)). Importantly, increased GABA-mediated inhibition is also observed in animal models of NF-1, and a corresponding inhibition of the Ras activity in the NF-1 animals attenuates the increased GABA-inhibition and rescues the decreased LTP (Costa, R. M. et al., $Nature$ 415(6871):526-30 (2002)).

Another class of identified genetic abnormalities affecting cognitive processes is single gene mutations that result in mental retardation. These disorders may be further divided into syndromic and non-syndromic mental retardation (MR), where in non-syndromic MR the cognitive impairment is the only identified phenotype whereas syndromic MR shows other phenotypes, such as unique facial profiles, underdeveloped limbs, and other physical characteristics.

A single gene mutation resulting in a syndromic MR that may be treated with the inhibitor compounds is Neurofibromatosis-1 (NF-1), a common genetic disorder caused by mutations in the gene encoding neurofibromin. The protein neurofibromin has several biochemical functions, including Ras GTPase-activation, adenyl cyclase modulation, and microtubule binding, and is expressed in a variety of different cell populations. Activation of Ras in NF-1 is associated with increased cell proliferation, and mutations in neurofibromin are shown to predispose the subject to certain types of cancers. In addition to the increased incidence of cancers, NF-1 affected subjects also show a broad range of both nonverbal and verbal learning disabilities (Costa R M et al., *Trends Mol Med.* 9(1):19-23 (2003)). Children with NF-1 display an increased frequency of mental retardation (Wechsler Full-Scale IQ<70) and have specific deficits in visual-spatial ability, executive function, expressive and receptive language, and attentional skills. The underlying cause of the cognitive deficits in subjects with NF-1 defects is unclear because of the multiple functions associated with the protein (see, e.g., U.S. Pat. No. 6,356,126). Although farnesyl transferase inhibitors have been shown to improve the learning deficits in animal models of NF-1 (Costa, R. M. et al., *Nature* 415(6871):526-30 (2002)), inhibiting the farnesyl lipid attachment pathway is demonstrated to cause compensating increases in geranylgeranylation pathway (Du, W. et al., *Mol Cell Biol.* 19(3): 1831-40 (1999)). Thus, results from use of farnesyl transferase inhibitors are not predictive of the effect HMG CoA reductase inhibitors, which would affect both farnesylation and geranylgeranylation of proteins. Evidence presented herein using HMG CoA reductase inhibitors suggest that the activity of Ras is responsible for the various cognitive deficits associated with NF-1.

In yet other embodiments, the syndromic MR is tuberous sclerosis complex (TSC), an autosomal dominant disease characterized by mental retardation, seizures, and tumors of various organs, including the kidney, brain, heart, and skin. Thus, TSC appears to act as a tumor suppressor gene. The TSC complex is composed of TSC1, which encodes hamartin, a protein of unknown function, and TSC2 gene product termed tuberin, which is a GTPase activating protein that is known to affect the Ras family GTPases, Rap1 and Rab5 in vitro. Since deleting TSC may result in over activation of MAPK (see Karbowniczek et al., *J. Biol. Chem.* 279(29): 29930-7 (2004)), statins, which can decrease MAPK activity, could be used to treat this disorder.

Another type of genetic abnormality affecting cognitive functions is non-syndromic MR, also referred to as non-specific MR. Affected patients have no distinctive clinical or biochemical features other than the cognitive deficit. A number of X-linked chromosomal genes mutated in nonspecific MR have been identified. These include, among others, FMR2, GDI1, RPS6KA3, IL1RAPL, TM4SF2, OPHN1 and PAK3. Cognitive deficits associated with mutations in the gene encoding OPHN1 (Oligopherin) may be treated with the compounds disclosed herein.

OPHN1 encodes a protein related to Rho-GTPase-activating protein (RhoGAP) (van Galen, E. J. et al., *Prog Brain Res.* 147:295-317 (2005)). By enhancing their GTPase activity, GAP proteins inactivate Ras and Ras related proteins, such as Rho. Consequently, inactivation of RhoGAP proteins is believed to cause constitutive activation of their GTPase targets (Billuart, P. et al., *Nature* 392(6679):923-6 (1998)). OPHN1 is expressed in both glial and neuronal cells and is shown to colocalize with actin at the tip of growing neurites. In addition to the cognitive deficits, subjects with OPHN1 mutations display epileptic seizures, ataxia, and cerebellar hypoplasia.

Although the various embodiments of cognitive disorders described above have a known biological foundation, it is to be understood that the methods disclosed herein may be used for a recognized and diagnosable cognitive disorders for which there are no identified biological cause. The cognitive deficits and associated symptoms seen in the disorders arising from identified genetic abnormalities appear in some instances to overlap with the features of cognitive disorders of unknown etiology. For instance, enhanced sensitivity to startle stimuli is seen in Coffin Lowry syndrome but also in ADHD. There is also a high incidence of ADHD in NF-1 patients, suggestive of a correlation of ADHD and the underlying biological defects in Coffin-Lowry syndrome and/or NF-1 (Schrimsher, G. W, et al., *Am. J. Med. Genet.* 120(3): 326-30 (2003)). Another example of this overlap is seen in Angelman syndrome, Down syndrome, or TSC patients, who display characteristic impairments in language ability, adaptive behavior, and cognition found in autism (Peters, S. U. et al., *Clin Genet.* 66(6):530-6 (2004); Kent L, et al., *Dev. Med. Child Neurol.* 41(3):153-8 (1999)).

Thus, in some embodiments, the cognitive disorder treatable with the inhibitor compounds may be ADHD. ADHD is a behavioral condition of childhood, affecting 5-10% of school-age children. Affected patients exhibit various behavioral problems such as carelessness, restlessness, disobedience and failure to stay quiet in class. As noted below, ADHD is diagnosed when the subject suffers from levels of inattention and/or hyperactivity-impulsivity that has persisted for more than 6 months and is maladaptive or inconsistent with the developmental level observed in the general population. Working memory appears to be impaired in ADHD (Westerberg, H. et al., *Neuropsychol. Dev Cogn. C Child Neuropsychol.* 10(3):155-61 (2004)). The most common pharmacologic therapy for ADHD is stimulants or stimulant mixtures, such as Ritaline® (methyphenidate), Adderall®, pemoline, or dextroamphetamine. It is believed that stimulants affect nonepinephrine and dopamine pathways, thereby providing impulse control and working memory. For those individuals who do not respond to treatments with stimulants, alternative treatments include use of antidepressants (e.g., desipramine, imipramine, nortyptiline, bupropione) and $\alpha_2$-agonists (e.g., clonidine and guanfacine). Use of the inhibitor compounds described herein may provide an alternative therapy for ADHD.

In other embodiments, the cognitive disorder that may be treated is autism. Criteria for the diagnosis of autism is given in the ICD-10 (International Classification of Diseases, 10th Revision) and the *Diagnostic and Statistical Manual of Mental Disorders,* 4th Ed. (DSM-IV). Though a complex disorder, autism has identifiable characteristics that include qualitative impairments in social communication, social interaction, social imagination, with a restricted range of interests and stereotyped repetitive behaviors and mannerisms. Affected individuals also show sensory hyposensitivities or hypersensitivities (Herault J. et al., *Am J Med Genet.* 60(4):276-81 (1995)). Epilepsy occurs more commonly than usual in autism. As discussed above, autism has been associated with many cytogenetic abnormalities, including Angelman syndrome, TSC syndrome, and thus provides a basis for extension of the treatments herein to cognitive deficits associated with autism.

As is apparent from the foregoing descriptions, dysfunction of basic cellular processes underlie many known forms of cognitive disorders. Consequently, any cognitive deficits arising from same underlying molecular mechanism may also be treated using the inhibitor compounds described herein. Accordingly, in some embodiments, the HMG CoA reductase inhibitors and other inhibitor compounds are used to treat cognitive deficits associated with dysregulation of small monomeric GTP binding proteins and proteins that regulate or are the targets of the signal transduction pathway regulated by these proteins. For instance, the role of Ras mediated signaling in synaptic plasticity and learning and memory is underscored by the observed effect of Ras in synaptic plasticity and a role for Rap, Rab and Rac in LTP (Murray, H. J. et al., *Brain Res.* 1000(1-2):85-91 (2004)). Both the overactivation and underactivation of Ras and related pathways appear to affect learning and memory.

"Small monomeric GTP binding protein" as used herein refers to a protein that binds guanine nucleotides (GTP and GDP), generally has an associated GTPase activity, and displays homology to Ras protein sequence. The term "Ras-related protein" will refer to a small monomeric GTP binding protein with sequence homology to Ras. The Ras-related proteins typically have a sequence motif involved in binding to guanine nucleotides, a carboxy terminal domain for post-translocation modification with farnesyl, geranylgeranyl, palmitoyl, or methyl moieties (e.g., a Cys-A-A-X, where A is aliphatic and X is any amino acid; Cys-X-Cys; and Cys-Cys), and in some instances, a domain that interacts with guanine nucleotide exchange factors (GEFs). Small monomeric GTP binding proteins may be categorized into subfamilies that include, by way of example and not limitation, the proteins within groups designated as Ras, Rho, Rab, Sar1/Arf and Ran. The Ras subfamily of proteins includes c-Harvey (H)-ras, c-Kirsten (K)-ras, and N-ras. The Rho subfamily includes Rho, Rac, and Cdc42.

Homology between small monomeric GTP binding proteins is about 30% or more amino acid identity. For example, Ras proteins share about 30% amino acid identity with Rab, Rho, Rac, and Cdc42. Proteins within a particular subgroup may have higher sequence homology (e.g., more than 50% amino acid identity) than between subgroups. The terms "percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, *Adv. Appl. Math.* 2:482 (1981), by the homology alignment algorithm of Needleman and Wunsch, *J. Mol. Biol.* 48:443 (1970), by the search for similarity method of Pearson and Lipman, *Proc. Nat'l. Acad. Sci. USA* 85:2444 (1988), by computerized implementations of these algorithms (GAP, BESTFIT, FASTA, and TFASTA in the GCG Wisconsin Software Package), or by visual inspection (see generally, *Current Protocols in Molecular Biology*, F. M. Ausubel et al., eds., Greene Publishing Associates, Inc. and John Wiley & Sons, Inc., (1995 Supplement). Examples of algorithms that are suitable for determining percent sequence identity and sequence similarity are the BLAST and BLAST 2.0 algorithms, which are described in Altschul et al. *J. Mol. Biol.* 215: 403-410 (1990) and Altschul et al. *Nucleic Acids Res.* 3389-3402 (1977), respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (Henikoff et al., *Proc. Natl. Acad. Sci. USA* 89:10915 (1989)).

All of the above mentioned algorithms and programs are suitable for a determination of sequence alignment and % sequence identity, for determination of % sequence identity in connection with the small monomer GTP binding proteins. Exemplary programs for determining the % sequence identity or homology may use the BESTFIT or GAP programs in the GCG Wisconsin Software package (Accelrys, Madison Wis.), using default parameters.

In some embodiments, the present disclosure provides methods of treating cognitive deficits associated with dysregulation of Ras protein activity, such as N-ras and K-ras. Ras proteins transmit extracellular signals that promote the growth, proliferation, differentiation, and survival of cells. Extracellular signals generate an intracellular signal that, in some instances, leads to activation of gunanine nucleotide exchange factors (GEF), and subsequent activation of Ras. Regulation of MAPK by Ras is believed to occur through Raf, which is activated on the plasma membrane by Ras-GTP. Raf phosphorylates mitogen-activated kinase 1/2 (MEK1/2 kinase), which activates the extracellular-regulated kinase 1/2 (ERK1/2 kinase or p44/42 MAPK) by phosphorylation. ERK1/2 kinase phosphorylates a variety of downstream targets, which results in changes in gene expression and the activities of other proteins. Mutations in genes encoding members of the MAPK pathway, such as MEK, Ras-GRF, and H-Ras, may cause defects in learning and LTP (Brambilla, R. et al., *Nature* 390:281-286 (1997); Atkins, C. M. et al., *Nat. Neurosci.* 1:602-609 (1998); Manabe et al., *J. Neurosci.* 20:2504-2511 (2000), and may couple metabotropic glutamate receptor activity to regulation of CREB transcription factor activity (Tian, X. et al., *EMBO J.* 23(7):1567-1575 (2004)).

In other embodiments, the cognitive deficit is associated with dysregulation of Rho protein activity. Rho proteins participate in various cellular processes such as cytoskeletal reorganization, membrane trafficking, transcriptional activation, and cell growth regulation. Mechanistically, Rho protein is thought to act by binding to target proteins that include Rho-kinase, myosin light chain, and protein kinases PKN and PRK2. Rho is believed to be regulated by Rac. Involvement of Rho protein in actin reorganization may indicate a role in both pre- and post-synaptic morphological changes. In addition, modulation of Rho activity appears to reduce or enhance LTP in vitro (O'Kane, E. M. et al., *Neuropharmacology* 46(6): 879-87 (2004)). Thus, the HMG CoA inhibitor compounds may be used to treat cognitive deficits that arise from dysregulation of Rho protein activity.

In some embodiments, the treatment is directed to cognitive deficits associated with dysregulation of Rac proteins, which play a role in stimulating the formation of lamellipodia and membrane ruffles. Among the effectors of Rac activity are serine/threonine kinases known as PAKs, one of which (i.e., PAK3) is associated with X-linked MR. In some instances, targeted inhibition of Rac in vitro produces enhanced LTP in hippocampal cultures (O'Kane, E. M. et al, supra). Thus, overactivation or underactivation of Rac may result in cognitive deficits.

In other embodiments, the treatment is directed to cognitive deficits associated with dysregulation of Rab protein, which regulates vesicle formation, actin- and tubulin-dependent vesicle movement, and membrane fusion. Rab proteins may be categorized based on function into two groups: (1) proteins involved in regulated secretion and (2) proteins involved in vesicle transport. For instance Rab3A is involved in regulated exocytosis of neurotransmitters and thus may contribute synaptic plasticity. In animal models, elimination of Rab3A function affects short and long-term synaptic plasticity in the mossy fiber pathway and altered circadian motor activity, but show no effects on spatial learning. Rab3A deleted animals, however, are moderately impaired in reference memory, show deficits in spatial working memory, have increased locomotor activity, and display enhanced exploratory activity (D'Adamo, P. et al., *Eur J Neurosci.* 19(7): 1895-905 (2004)).

In further embodiments, the inhibitors compound are used to treat cognitive deficits associated with dysregulation of Rap protein, a Ras-like GTPase that is localized in endocytic and lysosomal vesicle. Rap is a target of protein kinase A and may act as an antagonist of Ras activity by interacting with and trapping Raf1, a Ras effector, in an inactive complex. It may also function independently of Ras to regulate MAPK pathway (Asha, H. et al., *EMBO J.* 18(3):605-15 (1999)). The antagonistic activity of Rap1 suggests that lack of Rap1 function may result in enhanced Ras signaling.

In additional embodiments, the inhibitor compounds are used to treat cognitive deficits associated with dysregulation of Ral proteins, a downstream effector of Ras. In addition to its role in Ras pathway, Ral may also be activated by Ras independent pathway. Ral GTPases, RalA and RalB, appear play a role in vesicle regulation since they are present at high levels in synaptic vesicles; participate in the regulation of Arf-dependent phospholipase D (PLD), an enzyme implicated in vesicle function; and regulate RalBP1, which forms a complex with proteins involved in clathrin-mediated endocytosis. In animals with inactive Ral pathway, there is suppression of protein kinase C-mediated enhancement of glutamate secretion, indicating a role of Ral in modulating synaptic strength, a key component of LTP.

Activity of small monomeric GTP binding proteins is regulated by proteins that affect the GTP/GDP bound form. Accordingly, in some embodiments, the cognitive deficit treatable by the inhibitor compounds is associated with dysregulation of a GPTase activating protein (GAP). GAP proteins interact directly with Ras and Ras-related proteins to enhance the intrinsic rate of hydrolysis of bound GTP. Loss of function of GAP may result in an increase in GTP bound forms of guanine nucleotide binding proteins, thereby increasing the activity of proteins such as Ras, Rac, and Rho. For example, activity of Rho protein affected by 190Rho-GAP appears to be involved in memory formation in the amygdala (Lamprecht, R. et al., *Neuron.* 36(4):727-38 (2002)). In addition, the Rho-GTPase activating enzyme MEGAP/srGAP is show to be affected in X-linked mental retardation (Endris V. et al., *Proc Natl Acad Sci USA* 99(18): 11754-9 (2002)). In some embodiments, the dysregulation is in the Ras-GAP protein Neurofibromin-1 (Costa, R. M. et al., *Nature Genetics* 27:399-405 (2001)). In other embodiments, the dysregulation is in Rho-GAP, such as OPHN1 noted above.

In other embodiments, the inhibitor compounds are used to treat cognitive deficits associated with dysregulation of a guanine nucleotide exchange protein (GEP), also referred to as guanine nucleotide release factor (GRF) or guanine nucleotide exchange factor (GEF). GEFs may be specific to certain small monomeric GTP binding proteins, such as Ras, or have wider specificity, such as GEFs that active Rho, Rac and Cdc42. These regulators of Ras and Ras-related proteins enhance the exchange of bound GDP for GTP, thereby activating the Ras or Ras-related proteins. Thus, loss of GEF function would result in reduction in Ras or Ras-related protein activity, which has been correlated with loss of learning and memory. However, in some instances, Ras can also activate GEFs that target other Ras-related proteins. For instance, GTP bound forms of Ras and Rap1 interact with RalGEF to activate its GEF activity directed against Ral, thereby activating Ral activity (Giese, K. et al., *Neuropharmacology* 41, 791-800 (2001)). Accordingly, cognitive deficits arising from changes in GEF activity could be treated with HMG CoA reductase inhibitors and other inhibitor compounds described herein.

In other embodiments, the cognitive deficit is associated with dysregulation of guanine nucleotide dissociation inhibitors (GDI). This regulator of Ras-like protein inhibits dissociation of GDP, thereby maintaining a pool of GDP bound small monomeric GTP binding proteins. GDIs are known to regulate the activities of Ras, Rab, Ran, and Rho. For instance, GDI affects state of Rab and also functions in the vesicular transport of Rab GTPases through the secretory pathway by altering the cytosolic and membrane localization of Rab. GDIs are know to affect learning and memory. For example, model animals systems with deletion of GDI1 displays impairment in tasks requiring formation of short-term temporal associations, suggesting a defect in short-term memory. The animals also show lowered aggression and altered social behavior (D'Adamo, P. et al., *Human Molecular Genetics* 11(21):2567-2580 (2002)). Thus, GDI may act to suppress hyperexcitability in neurons since loss of GDI1 function appears to produce hyperexcitability, a consequence of which is an increase in epileptic seizures.

In other embodiments the cognitive deficit is associated with dsyregulation of a target of Ras or Ras-related protein activity. In some embodiments, the treatments with inhibitor compounds are directed to cognitive deficits associated with dysregulation of Raf, a downstream effector of Ras. Raf encodes a serine threonine kinase and is believed to be activated by direct interaction with Ras. Activation of Raf1 by Ras leads to activation of the MAPK pathway, which in hippocampal cultures is thought to be involved in establishment LTP. Further, as disclosed herein, hyperactivation of MAPK pathway by Ras signaling is observed in animal models of NF-1.

In some embodiments, the present disclosure also provides use of the inhibitor compounds to treat cognitive deficits arising from dysregulation of MAPK signaling pathway. Genetic and biochemical studies implicate components of the MAPK signaling pathway in cognitive function. For example, Ras in NF-1 appears to act through modulation of the MAPK pathway. In addition, extracellular-regulated receptor kinases (ERK) may be involved in regulating downstream CREB activity and modulating synaptic structure (Sweatt, J. D. et al., *Curr. Opin. Neurobiol.* 14(3):311-7 (2004)). As used herein, "MAPK signaling pathway," some of which have been described in various parts of this disclosure, refers to a signaling pathway that uses a cascade of three types of kinases, also referred to as the "MAPK module." These canonical kinases include a MAP kinase kinase kinase (MAPKKK), which activates a second kinase, the MAP kinase kinase (MAPKK) by phosphorylation of serine/threonine residues. MAPKKs are dual specificity kinases capable of phorphorylating both serine/threonine and tyrosine residues. Activated MAPKKs modify MAP kinases (MAPK) by phosphorylation of both threonine and tyrosine residues. In turn, the MAPKs regulate activity of other protein kinases and numerous transcription factors to effect the cellular responses triggered by activation of the signaling cascade. Three distinct pathways form the superfamily of MAPK pathways, each designated based on the MAPK involved. The p38/HOG pathway uses p38/HOG MAPKs, which are activated by dual specificity kinases MEK3/MKK4. The corresponding MAPKKK for this pathway appears to be TAO-1. The second MAPK pathway, also known as the stress activated protein kinase pathway, uses c-jun N-terminal kinase (JNK) MAPKs, which are activated by dual specificity kinases MEK4/JNK kinase. The corresponding MAPKKK for the JNK pathway is MEKK. The third pathway and the best characterized uses a MAPK referred to as extracellular signal-regulated kinases (ERK), of which ERK1 and ERK2 are members. Dual specificity kinases of the ERK pathway include MEK1 and MEK2, which are targets of Raf, a MAPKKK. As explained in the previous sections, the ERK pathway is believed to be directly involved in learning and memory via the action of Ras on Raf. Evidence for involvement of the other MAPK pathways in cognitive function come from use of selective inhibitors of JNK and p38 pathways. Selective inhibition of p38 pathway affects associative learning and memory formation (Zhen, X. et al., *J Neurosci.* 21(15):5513-9 (2001); Alonso, M. et al., *Neuroreport* 14(15):1989-92 (2003)) while selective inhibition of JNK blocks long term memory (Bevilaqua, L. R. et al., *Eur. J. Neurosci.* 17(4):897-902 (2003)). Rac and its downstream effectors, p21 activated kinases (PAK), are known to regulate the p38 and JNK MAPK pathways. Thus, cognitive deficits arising from dysregulation of p38 and JNK signaling pathways by altered activity of Rac and other small monomeric GTP binding proteins may be treated with the inhibitor compounds.

In other embodiments, the cognitive deficit is associated with dysregulation of inhibitory neuronal activity. "Inhibitory neuronal activity" as used herein refers to activity that opposes or inhibits excitation of a neuron. Generally, inhibitory neuronal activity may occur presynaptically, such as attenuating or inhibiting release of excitatory neurotransmitters, or occur postsynaptically by attenuating or preventing the excitatory neurotransmitter from activating the postsynaptic neuron. In some embodiments, the inhibitory neuronal activity is an inhibitory postsynaptic potential (IPSP), which lowers the membrane potential of the postsynaptic neuron, thereby reducing the probability of the postsynaptic neuron from generating an excitatory postsynaptic potential (ESPS).

In some embodiments, the dysfunction in the inhibitory neuronal activity is associated with increased GABA-mediated inhibition. In the GABA pathway, inhibitory neurons package the neurotransmitter GABA in synaptic vesicles and release it upon activation of the inhibitory neuron. GABA discharged into the synaptic cleft is recognized by GABA receptors, whose activation inhibits an excitatory signal in the postsynaptic neuron. The principle GABA receptors are $GABA_A$ and $GABA_B$, although other GABA type receptors that are known to act in inhibiting neuronal activity are to be included within this class. The $GABA_A$ receptors are members of the Cys-loop superfamily of ligand gated ion channels that includes the receptors for glycine, acetylcholine, and 5-HT3. $GABA_A$ receptors are known for their interaction with benzodiazepine type agonists. Structurally, the $GABA_A$ receptor is a heteromultimeric protein, generally composed of five subunits that come from at least four principle families of subunits α, β, γ, and δ, but which may include other subunits, such as π, θ, and ε. Typically, each subunit transverses the postsynaptic membrane and interacts to form a central pore, which, when opened, allows for the passage of chloride ions into the neuron. Thus, $GABA_A$ type receptors are ionotropic receptors. Activation of the $GABA_A$ receptor by binding of GABA results in increased inward chloride ion flux and hyperpolarization and subsequent neuronal inhibition. $GABA_B$ receptors also bind GABA, but are G-protein coupled receptors (GPCRs) that modulate $Ca^{+2}$ or $K^+$ ion channel activity and various second messenger pathways. $GABA_B$ receptors are heteromeric proteins, typically a dimer, and like other GPCRs, characterized by the presence of seven transmembrane spanning regions. Of the various families of GPCRs, $GABA_B$ receptors are categorized within Family 3, the members of which are defined by the presence of a ligand binding domain in the large extracellular amino terminal region. In addition to $GABA_B$ receptors, exemplary members of Family 3 GPCRs include, by way of example and not limitation, metabotropic glutamate receptors, $Ca^{+2}$ receptors, taste receptors, and odorant receptors. Without being bound by theory, $GABA_B$ receptors are believed to mediate neuronal inhibition by activation of inwardly rectifying potassium channels (GIRKS) resulting in hyperpolarization in the postsynaptic membrane. In the presynaptic membrane, $GABA_B$ is thought to inhibit presynapstic $Ca^{+2}$ channels, thereby causing inhibition of neurotransmitter release. Overactivation of GABA-mediated inhibition correlates with impaired cognitive function in NF-1 and Down Syndrome. For NF-1, the associated depressed LTP is ameliorated by inhibition of RAS activity and by attenuation of GABA mediated inhibition by the GABA antagonist picrotoxin. As shown herein, HMG CoA reductase inhibitors not only reverse the cognitive deficits in animal models of NF-1 but also enhances the LTP response, indicative of attenuation of GABA mediated inhibition.

In some embodiments, the inhibitor compounds are used to modulate the underlying cellular processes associated with cognitive function. As noted above, the phenomena of LTP in neural cultures, typically a hippocampal system, is widely held as being a molecular correlate of the processes involved in short term and long-term memory. LTP occurs at all three major synaptic connections in the hippocampus, including: the perforant path synapse to dentate gyrus granule cells, mossy fibers to CA3 pyramidal cells, and the Schaffer collaterals of CA3 cells to CA1 pyramidal cells. There are at least two art-recognized forms of LTP that are temporally related to each other. An early-phase LTP or E-LTP has the characteristics of being independent of transcription and protein synthesis, and decays within 1-3 h of induction. This short lasting LTP is considered as the molecular correlate to short-term memory. The second form of LTP, referred to as late phase LTP or L-LTP, requires transcription and translation and can persist for hours or days. L-LTP is believed to be cellular counterpart of long-term memory storage. Both forms of LTP may be generated in hippocampal cultures by stimulation of a single input pathway (i.e., homosynaptic) by a train of evoked potentials. E-LTP is typically induced by a single high-frequency tetanic stimulus whereas L-LTP is typically induced by multiples (e.g., three to four) of such tetanic trains (see, e.g., Thomas, M. J. et al., *J Neurosci.* 18:7118-7126 (1998)). L-LTP may also be induced by paired stimulation of multiple input pathways (i.e., heterosynaptic), where activation of one afferent pathway is paired to a conditioning stimulus in another afferent pathway in the neural network (Huang, Y. Y. et al., *Proc. Natl. Acad. Sci. USA* 101(3):861-864 (2004)). Timing of the paired stimulus appears critical for generating L-LTP in the heterosynaptic system.

Since HMG CoA reductase inhibitors appears to show now measurable effect on subjects with normal cognitive function, the neural systems on which the inhibitors may be used will typically have a depressed LTP. As used herein, a "depressed LTP" refers to a lower LTP response than measured for another subject. An exemplary depressed LTP is that observed for a subject with a genetic defect affecting LTP, where the LTP in the affected subject is lower than what is observed for a subject without the genetic defect. Similarly, another exemplary depressed LTP is that observed when the neural system is treated with a pharmacological agent that reduces the LTP response as compared to a subject that has not been treated with the pharmacological agent.

For modulating the LTP of neural networks, the neural system is contacted with an effective amount of an inhibitor compound. "Modulate" as used herein refers to inhibition or enhancement of the LTP in the neural system being examined when compared to the LTP in the absence of such compounds. In some embodiments, the neural system may have an underlying deficit in cognitive function, which may be reflected in the LTP. The LTP affected may be the early phase E-LTP, but more typically late phase or L-LTP. Dysregulation of the cellular processes associated with altered LTP include genetic defects induced in model animal systems or those found naturally in animals and humans, or various in vitro manipulations that disrupt a cellular process. Exemplary manipulations of in vitro systems to alter LTP include overexpression of a target protein (e.g., small monomeric GTP binding protein), expression of proteins with dominantly acting mutations (e.g., dominant negative or dominant active), use of inhibitors of enzyme activity (e.g., protein kinase inhibitors, ubiquitin mediate protein degradation inhibitors, toxins to inhibit small monomeric GTP binding proteins), and silencing of expression of target genes (e.g., using interfering RNA, anti-sense RNA, etc.). Other manipulations will be apparent to the skilled artisan. It is to be understood that the LTP resulting from the dysfunction or dysregulation of processes described in the preceding sections may be modulated by using the inhibitor compounds.

6.2 HMG CoA Reductase Inhibitors, Compositions, and Inhibitor Combinations for the Treatment of Cognitive Disorders Treating the cognitive deficits associated with the disorders described above comprises administering a HMG CoA reductase inhibitor to a subject in an amount effective to improve, enhance, or restore cognitive function. As used herein, an "HMG CoA Reductase inhibitor" is any compound or composition, including prodrugs, salts, solvates and hydrates thereof, that inhibits HMG CoA reductase activity. An inhibitor includes compound that act via competitive, non-competitive, or un-competitive mechanisms, as they are commonly known in the art. One important class of HMG CoA reductase inhibitors are generally known as statins, which are prescribed to treat hyperlipidemia characterized by elevated serum cholesterol levels.

Various HMG CoA reductase inhibitors, corresponding prodrugs, salts, solvates and hydrates, are known in the art and may be used for the methods herein. Atorvastatin and derivatives thereof are described in U.S. Pat. No. 5,273,995 and EP 409281 and are available commercially under the tradenames Lipitor®, Sortis®, Torvast®, Totalip®, and Xarator®. Cerivastatin and derivatives thereof are described in U.S. Pat. Nos. 5,006,530; 5,177,080, and EP 325130 and are available under the tradenames Rivastatin®, Baycol®, and Lipobay®. Although the levels of cerivastatin prescribed for hyperlipidemia has resulted in toxic side effects, lower non-toxic levels may be appropriate for treatment of cognitive deficits.

Another of these statin compounds is clofibrate and derivatives thereof, as described in U.S. Pat. No. 3,262,850 and GB 860303. Clofibrate is available under the tradenames Amotril®, Anparton®, Apolan®, Artevil®, Claripex®, Liprinal®, Normet®, Regelen®, Serotinex®, and Xyduril®. Inhibitor colestipol and derivatives thereof are described in U.S. Pat. Nos. 3,692,895 and 3,803,237 and published patents DE 1927336, and DE 2053585. Fluvastatin and derivatives thereof are described in U.S. Pat. No. 4,739,073 and WO 84/02131 and are available under the tradenames Fluindostatin®, XU 62-320, Lescol®, Lipaxan® and Primexin®. Gemfibrozil and derivatives thereof are described in U.S. Pat. Nos. 3,674,836 and 4,126,637, and published patent DEL 1925423, and are available under the tradenames Decrelip®, Genlip®, Gevilon®, Lipozid®, and Lopid®. Lovastatin and derivatives thereof are described in U.S. Pat. No. 4,231,938. and are available under the tradenames Altocar®, Lovalip®, Mevacor®, Mevinacor®, Nevlor®, and Sivlor®. Pitavastatin and derivatives thereof are described in EP65835 and U.S. Pat. No. 6,162,798 and are available under the tradenames Itabastatin®, Livalo®, Nisvastatin®, Itavastatin®, and Zomaril®. Pravastatin and derivatives thereof are described in U.S. Pat. No. 4,346,227 and published patent DE 3122499, and are available under the tradenames Elisor®, Lipostat®, Liprevil®, Mevalotin®, Oliprevin®, Pravachol®, Pravasin®, Selectin®, and Vasten®. Rosuvastatin and derivatives thereof are described in U.S. Pat. Nos. 5,128,366, 6,589,959, and published application WO 521471, and are available under the tradename Crestor®. Simvastatin and derivatives thereof are described in U.S. Pat. No. 4,444,784 and EP 33538 and are available under the tradenames Denan®, Liponorm®, Simovil®, Sinvacor®, Sivastin®, Zocor®, and Zocord®.

It is to be understood that while a single inhibitor is typically prescribed to lower elevated cholesterol levels, mixtures of HMG CoA reductase inhibitors may be used for the uses described herein. Compatible mixtures may be made to enhance the efficacy and/or lower the toxicity of the inhibitors in treating the cognitive disorders.

In some embodiments, other compounds targeting the cholesterol biosynthetic pathway may be used to treat the cognitive deficit. Thus, in some embodiments, the compound is a modulator of farnesyl transferase, such as an inhibitor of farensyl transferase activity. As used herein, a farnesyl transferase inhibitor is an inhibitor of the enzyme responsible for transfer of farnesyl pyrophosphate onto protein substrates. Suitable farnesyl transferase inhibitors include, by way of example and not limitation, FTI-276 (Calbiochem, San Diego, Calif., USA); SCH66336 (Schering-Plough, (Kenilworth, N.J., USA); (B)-6-[amino(4-chlorophenyl)(1-methyl-1H-imidazol-5-yl)methyl]-4-(3-chlorophenyl)-1-methyl-2 (1H)-quinolinone (also known as R115777, tipifarnib, and Zarnestra) (Johnson & Johnson); L-778,123; and FTI-2148.

In other embodiments, the other compound may be a modulator of geranylgeranyl transferase activity, such as an inhibitor of geranylgeranyl transferase. These compounds may be suitable for cognitive disorders that are associated with dysregulation of Rac or Rho activity since these proteins are modified by attachment of geranylgeranyl groups. Suitable geranylgeranyl transferase inhibitors include, by way of example and not limitation, GGTI-286 (Calbiochem, San Diego, Calif., USA); GGTI-297; GGTI-2154; and GGTI-2166. Compounds with inhibitory activities to both farnesyl transferase and geranylgeranyl transferases are described in Tucker T. J. et al, *Bioorg. Med. Chem. Lett.* 12(15):2027-30 (2002)).

In some embodiments, the compounds that inhibit inhibitory neuronal activity may be used. A number of different aspects of inhibitory neuronal activity may be targeted, including, among others, transport of inhibitory neurotransmitters into synaptic vesicles, degradation of the inhibitory neurotransmitter, receptors that are activated by binding to inhibitory neurotransmitters, and channel proteins that decrease the generation of action potentials.

In some embodiments, the inhibitors inhibit GABA mediated inhibition, and thus are inhibitors of GABA receptor activity. An "inhibitor of GABA receptor" as used herein refers to a compound that binds to but does not activate GABA receptors (i.e., antagonists), thereby blocking the actions of endogenous GABA and GABA agonists. Also encompassed within "inhibitor of GABA receptor" is an inverse agonist, which binds to a region of the GABA receptor different from the region that interacts with GABA but which results in inhibition of GABA or GABA agonist binding. Useful inhibitors may have general activity against various forms of GABA receptors, or are selective for different GABA receptor types. Compatible mixtures of selective GABA receptor inhibitors may be used to generate a general inhibitor of GABA receptor activity.

Accordingly, in some embodiments, the inhibitor used is selective for $GABA_A$. Exemplary embodiments of antagonist compounds selective for $GABA_A$ receptor include, by way of example and not limitation, picrotoxin; hydrastine; securinine; 6-(5,6,7,8-tetrahydro-6-methyl-1,3-dioxolo[4,5-g]isoquinolin-5-yl)furo[3,4-e]-1,3-benzodioxol-8(6H)-one (i.e., bicuculline); 6-Imino-3-(4-methoxyphenyl)-1(6H)-pyridazinebutanoic acid hydrobromide (i.e., gabazine); 4-(2-naphthylmethyl)-5-(4-piperidyl)-3-isoxazolol and analogs thereof (Frolund, B. et al., *J. Med. Chem.* 48(2):427-39 (2005)); β-carboline-3-carboxylate-t-butyl ester (Rowlett J, et al., *CNS Spectr.* 10(1):40-8 (2005). $GABA_A$ inverse agonists include the naturally occurring peptide Diazepam Binding Inhibitor (DBI); methyl-6,7-dimethoxy-4-ethyl-beta-carboline-3-carboxylate (DMCM); ethyl-beta-carboline-3-carboxylate (beta-CCE), N-methyl-beta-carboline-3-carboxamide (FG 7142); ethyl-8-azido-5,6-dihydro-5-methyl-6-oxo-4H-imidazo [1,5 alpha][1,4]-benzodiazepine-3-carboxylate (Ro 15-4513); (3-tert-Butyl-7-(5-methylisoxazol-3-yl)-2-(1-methyl-1H-1,2,4-triazol-5-ylmethoxy)pyrazolo[1,5-d][1,2,4]triazine; and 2-methoxy-3,8,9-trihydroxy coumestan (PCALC36). Other $GABA_A$ antagonists and inverse agonists applicable to the uses herein will be apparent to the skilled artisan.

In other embodiments, the inhibitor used is selective for the $GABA_B$ receptor. Some exemplary embodiments of antagonist compounds selective for receptor $GABA_B$ include by way of example and not limitation, 3-Amino-2-(4-chlorophenyl) propylphosphonic acid (i.e., phaclofen); 3-amino-2-(4-chlorophenyl)propylsulfonic acid (i.e., saclofen); 3-amino-2-(4-chlorophenyl)-2-hydroxypropyl-sulfonic acid (i.e., 2-hydroxysaclofen); 3-aminopropyl-diethoxymethylphosphinic acid (CGP 35348); 3-[[(3,4-dichlorophenyl)methyl]amino]propyl] diethoxymethyl)phosphinic acid (CGP 52432); (2S)-3-[[(1S)-1-(3,4-dichlorophenyl)ethyl]amino-2-hydroxypropyl](phenylmethyl)phosphinic acid (CGP 55845); 3-[[1-(S)-(3,4dichlorophenyl)ethyl]amino]-2-(S)-hydroxy-propyl]-cyclohexylmethyl phosplinic acid (CGP 54626); (3-aminopropyl)(cyclohexylmethyl)phosphinic acid (CGP 46381); and (2S)-(+)-5,5-dimethyl-2-morpholineacetic acid (SCH 50911). Other $GABA_B$ receptor inhibitors will be apparent to the skilled artisan.

In other embodiments, the inhibitors of HMG CoA reductase, farnesyl transferase inhibitors, and geranylgeranyl transferase, and inhibitors of inhibitory neuronal activity, (collectively referred to as "inhibitor compounds") may be used in combination to treat the cognitive disorder or modulate LTP. Combinations include a HMG CoA reductase inhibitor and a farnesyl transferase inhibitor, a HMG CoA reductase inhibitor and a geranylgeranyl transferase inhibitor, a farnesyl and geranylgeranyl transferase inhibitor, a HMG CoA reductase inhibitor in combination with farnesyl and geranylgeranyl tranferase inhibitors, or a HMG CoA reductase inhibitor in combination with an inhibitor of inhibitory neuronal activity. Other combinations will be apparent to the skilled artisan. While the combinations may be used generally for the cognitive disorders effectively treated by HMG CoA reductase inhibitors alone, some disorders may be treated with a specific combination where the molecular basis underlying the disorders is suggested as a farnesylated protein (e.g., RAS), a geranylgeranlylated protein (e.g., Rho or Rac), or a GABA receptor activity. For instance, learning disorders associated with NF-I may be treated with a combination of HMG CoA reductase inhibitor and a farnesyl transferase inhibitor or a HMG CoA reductase inhibitor and a $GABA_A$ receptor inhibitor.

The inhibitor compounds may be administered in the form of a composition. In other embodiments the inhibitor combinations are administered adjunctively, by the same route or by a different route. Adjunctive administration includes simultaneous or sequential administration of the inhibitor compounds.

The amounts of the inhibitor compounds to be administered will be determined empirically in accordance with conventional procedures. Generally, for administering the inhibitor compounds, the subject formulations are given at a pharmacologically effective dose. A "pharmacologically effective amount" or "pharmacologically effective dose" is an amount sufficient to produce the desired physiological effect or an amount capable of achieving the desired result, particularly for treating the disorder or condition, including reducing or eliminating one or more symptoms of the disorder or disease. Thus the compounds and compositions described herein may be administered therapeutically to achieve a therapeutic benefit or prophylactically to achieve a prophylactic benefit. By therapeutic benefit is meant eradication or ameliorating of the underlying disorder being treated, and/or eradication or amelioration of one or more of the symptoms associated with the underlying disorder such that the patient reports an improvement in cognitive function, notwithstanding that the patient may still be affected with the underlying disorder.

In the case of cognitive disorders, administration of the compounds and compositions to a patient suffering from the cognitive deficit provides a therapeutic benefit when there is improvement, enhancement, or restoration in the cognitive function. The compounds and compositions may also be administered prophylactically to a patient at risk of being afflicted with the cognitive disorder. For instance, these include individuals who have been diagnosed with an inherited disorder that has an associated disruption of normal cognitive function such that therapy may be initiated by early diagnosis (e.g., infancy).

A therapeutically effective dose of the inhibitor compounds is readily determined by methods well known in the art. Factors to consider in determining an appropriate dose include, but are not limited to, size and weight of the subject, the age and sex of the subject, the type of cognitive disorder, the severity of the cognitive disorder, method of delivery of the compounds and compositions, and half-life and efficacy of the inhibitor compounds.

An initial effective dose can be estimated initially from cell culture assays. For example, because the hippocampus is a model system for learning and memory, in vitro culture systems using hippocampal slices or cultures may be suitable for initial determination of an effective dose. The cells may be contacted with the inhibitor compounds and in the absence of inhibitor to determine the levels of drug useful for enhancing the cellular correlates of neural processes associated with cognitive function, such as LTP.

Following in vitro studies, a dose can then be formulated in experimental animal models to generate data on circulating concentration or tissue concentration, including that of the $IC_{50}$ (i.e., concentration sufficient to affect 50% of the activity being targeted or measured) as initially determined by the in vitro culture assays. Suitable experimental animals include, but are not limited to mouse, rat, guinea pigs, rabbits, pigs, monkeys and chimpanzees. As with the in vitro studies, initial determination is made of an effective dose of the inhibitor compound (e.g., $C_{max}$) and the corresponding pharmacokinetic profile. Useful in this regard are numerous identified animal model systems (e.g., pure bred animal lines) with associated cognitive disorder or transgenic (e.g., knockout) animals that mimic or approximate the genetic disorders that display the cognitive deficit. Behavioral tests can be conducted on these animal systems to determine an effective dose.

In accordance with the above, the dosages of the HMG CoA reductase inhibitors may be the standard dosages administered to treat hypercholesterolemia (i.e., an amount sufficient to lower serum cholesterol levels in a subject with hypercholesterolemia). Thus, an amount of inhibitor compound is used to lower the cholesterol level to those observed on or below the 95th percentile, on or below the 85th percentile, on or below the 75th percentile, on or below the 50th percentile of the subject population, to about 25th percentile of the subject population. In some embodiments, the amount of inhibitor compound is administered to lower the cholesterol level below about 240 mg/dL, below about 220 mg/dL, below about 200 mg/dL, below about 190 mg/dL, below about 180 mg/dL, or below about 170 mg/dL.

In other embodiments, an amount of HMG CoA reductase inhibitor is administered to lower the c-LDL levels to that below about the 95th percentile of the general population pool, below about the 85th percentile of the general population pool, below about the 75th percentile of the general population, below about the 50th percentile of the general population, to about the 25th percentile of the general population pool. Thus, in some embodiments, an amount of HMG CoA reductase inhibitor is administered to lower the c-LDL in a human subject to less than about 160 mg/dL, to less than about 130 mg/dL, to less than about 100 mg/dL, to less than about 70 mg/dL, with the lower limit being a level of LDL considered healthy, which may range from 40 mg/dL or 50 mg/dL for the human population.

Exemplary dosages for use of atorvastatin (Lipitor®) in the treatment of hypercholesterolemia are from about 10 mg to about 80 mg per day. For subjects of 45 to 100 kg body weight, this dosage corresponds to about 0.1 mg/kg/day to about 1.8 mg/kg/day. The recommended dosages of lovastatin (Mevacor®) is from about 10 mg to about 80 mg/day in one or two dosages, or about 0.1 mg/kg/day to about 1.8 mg/kg/day. The recommended dosage of rosuvastatin (Crestor®) is from about 5 mg to about 40 mg/day, or about 0.05 mg/kg/day to about 0.9/mg/kg/day. The recommended dosage for pravastatin (Pravachol®) is from about 10 mg to about 80 mg/day as a single dose, or about 0.1 mg/kg/day to about 1.0 mg/kg/day. The recommended dosage for simvastatin (Zocor®) is from about 5 mg to about 80 mg/day taken once per day, or about 0.05 mg/kg/day to about 1.8 mg/kg/day. Determining corresponding dosages for other HMG CoA reductase inhibitors are well within the skill of those in the art.

In other embodiments, dosages are lower than those prescribed to treat hypercholesterolemia or are dosages that do not result in significant lowering of serum cholesterol levels in the treated subject but which are effective in treatment of the cognitive deficit. These dosages are referred herein as "low dosages." In some embodiments, a significant lowering of cholesterol level is a change of about 5 percentile, 10 percentile, 15 percentile, 20 percentile, 30 percentile, 40 percentile of the cholesterol level in the general population. In other embodiments, a significant lowering of cholesterol level is change in serum or LDL cholesterol level of 20 mg/dL, 30 mg/dL, 50 mg/dL, 75 mg/dL or more. For atorvastatin or lovastatin, this may correspond to a dosage of from about 0.1 mg/kg/day to about 0.01 mg/kg/day or lower. For rosuvastatin and simvastatin, the lower dosage may correspond to a dosage of from about 0.05 mg/kg/day to about 0.005 mg/kg/day. Determining low dosages of all of the HMG CoA reductase inhibitors are well within the skill of those in the art.

The inhibitor compounds may be provided as various pharmaceutical compositions formulated in pharmaceutical compositions per se, or in the form of a hydrate, solvate, or pharmaceutically suitable salts thereof or with a suitable excipient. Accordingly, in one embodiment, the pharmaceutical compositions comprise a pharmaceutically acceptable carrier or vehicle and a pharmacologically effective amount of the inhibitor compound.

As described above, pharmaceutically acceptable salts are intended to include any art recognized pharmaceutically acceptable salt of the compound or inhibitor which is made with counterions understood in the art to be generally acceptable for pharmaceutical uses and which possesses the desired pharmacological activity of the parent compound. Examples of salts include sodium, potassium, lithium, ammonium, calcium, as well as primary, secondary, and tertiary amines, esters of lower hydrocarbons, such as methyl, ethyl, and propyl. Other salts include organic acids, such as acetic acid, propionic acid, pyruvic acid, maleic acid, succinic acid, tartaric acid, citric acid, benzoic acid, cinnamic acid, salicylic acid, etc.

As used herein, pharmaceutically acceptable vehicle or pharmaceutically acceptable carrier comprise any of standard pharmaceutically accepted carriers used by those skilled in the art for administering a pharmaceutical composition. Thus, the inhibitor compounds may be prepared as formulations in pharmaceutically acceptable excipients suitable for any mode of administration that include, but are not limited to, oral, topical, transdermal, cutaneous, subcutaneous, intravenous, intraperitoneal, intramuscular, nasal, transdermal, vaginal, buccal, and rectal (e.g., colonic administration) delivery. Choosing the appropriate route of administration is well within the skill of the art.

For oral administration, the pharmaceutical compositions may be prepared with pharmaceutically acceptable excipients such as binding agents (e.g., starch, carboxymethyl cellulose, hydroxylpropyl methyl cellulose), fillers (e.g., lactose, microcrystalline cellulose, calcium phosphate, etc.), lubricants (e.g., magnesium stearate, talc, silicon dioxide, etc.); disintegrants (potato starch and sodium starch glycolate); or wetting agents (e.g., sodium lauryl sulfate). Formulations for oral administrations may take various forms, including, but not limited to, tablets, capsules, lozenges, powders, etc. Pills, tablets, or capsules may have an enteric coating that remains intact in the stomach but dissolves in the intestine. Various enteric coatings are known in the art, a number of which are commercially available, including, but not limited to, methacrylic acid-methacrylic acid ester copolymers, polymer cellulose ether, cellulose acetate phathalate, polyvinyl acetate phthalate, hydroxypropyl methyl cellulose phthalate, and the like.

The inhibitors compounds may be in liquid form prepared in diluents for administration orally or by injection. These diluents include, by way of example and not limitation, saline, phosphate buffer saline (PBS), aqueous ethanol, or solutions of glucose, mannitol, dextran, propylene glycol, polyethylene glycol (e.g., PEG400), and mixtures thereof. Suitable diluents also include non-aqueous vehicles, including oils and other lipophilic solvents, such as various vegetable oils, animal oils, and synthetic oils (e.g., peanut oil, sesame oil, olive oil, corn oil, safflower oil, soybean oil, etc.); fatty acid esters, including oleates, triglycerides, etc.; cholesterol derivatives, including cholesterol oleate, cholesterol linoleate, cholesterol myristilate, etc.; liposomes; and the like. The compositions for injection may be prepared directly in a lipophilic solvent or preferably, as emulsions (see, e.g., Liu, F. et al., *Pharm. Res.* 12: 1060-1064 (1995); Prankerd, R. J. J., *Parent. Sci. Tech.* 44: 139-49 (1990); and U.S. Pat. No. 5,651,991). The formulations for injection may be presented in unit dosage form, e.g., in ampules or in multidose containers. The diluents may also contain suspending agents (e.g., soribitol solution, cellulose derivatives, or hydrogenated edible fats) and emulsifying agents (e.g., lecithin or acacia).

Formulations for rectal or vaginal administration may be in the form of salves, tinctures, crèmes, suppositories, enemas or foams. Suppositories for rectal application may contain conventional suppository bases such as cocoa butter, carbowaxes, polyethylene glycols, or glycerides, which are solid or semi-solid at room temperature but liquid at body temperature.

Additionally, the pharmaceutical compositions may include bactericidal agents, stabilizers, buffers, emulsifiers, preservatives, flavoring, sweetening agents, and the like as needed or desired in the various formulations.

The pharmaceutical compositions comprising the inhibitor compounds may be manufactured in a manner well known to the skilled artisan, such as by conventional means of mixing, dissolving, granulating, levigating, emulsifying, encapsulating, entrapping or lyophilization processes. Suitable pharmaceutical formulations and methods for preparing such compositions may be found in various standard references, such as *Remington's Pharmaceutical Sciences*, 17th edition, Mack Publishing Co., Philadelphia, Pa. (1985) and *Handbook of Pharmaceutical Excipients*, 3rd Ed, Kibbe, A. H. ed., Washington DC, American Pharmaceutical Association (2000); hereby incorporated by reference in their entirety.

Additionally, the inhibitors, either separately or as a combination, may also be introduced or encapsulated into the lumen of liposomes for delivery and for extending lifetime of the compounds. As known in the art, liposomes can be categorized into various types: multilamellar (MLV), stable plurilamellar (SPLV), small unilamellar (SUV) or large unilamellar (LUV) vesicles. Liposomes can be prepared from various lipid compounds, which may be synthetic or naturally occurring, including phosphatidyl ethers and esters, such as phosphotidylserine, phosphotidylcholine, phosphatidyl ethanolamine, phosphatidylinositol, dimyristoylphosphatidylcholine; steroids such as cholesterol; cerebrosides; sphingomyelin; glycerolipids; and other lipids (see, e.g., U.S. Pat. No. 5,833,948).

Cationic lipids are also suitable for forming liposomes. Generally, the cationic lipids have a net positive charge and have a lipophilic portion, such as a sterol or an acyl or diacyl side chain. Preferably, the head group is positively charged. Typical cationic lipids include 1,2-dioleyloxy-3-(trimethylamino)propane; N-[1-(2,3-ditetradecycloxy)propyl]-N,N-dimethyl-N-N-hydroxyethylammonium bromide; N-[1-(2,3-dioleyloxy)propyl]-N,N-dimethyl-N-hydroxy ethylammonium bromide; N-[1-(2,3-dioleyloxy) propyl]-N,N,N-trimethylammonium chloride; 3-[N-(N',N'-dimethylaminoethane) carbamoyl] cholesterol; and dimethyldioctadecylammonium.

Of particular interest are fusogenic liposomes, which are characterized by their ability to fuse with a cell membrane upon appropriate change in physiological condition or by presence of fusogenic component, particularly a fusogenic peptide or protein. In one aspect, the fusogenic liposomes are pH and temperature sensitive in that fusion with a cell membrane is affected by change in temperature and/or pH (see for example, U.S. Pat. Nos. 4,789,633 and 4,873,089). Generally, pH sensitive liposomes are acid sensitive. Thus, fusion is enhanced in physiological environments where the pH is mildly acidic, for example the environment of a lysosome or endosome. This property allows direct release of the liposome contents into the intracellular environment following endocytosis of liposomes (Mizoue, T., *Int. J. Pharm.* 237: 129-137 (2002)).

Another form of fusogenic liposomes comprises liposomes that contain a fusion-enhancing agent. When incorporated into the liposome or attached to the lipids, the agents enhance fusion of the liposome with other cellular membranes, thus resulting in delivery of the liposome contents into the cell. The agents may be fusion enhancing peptides or proteins, including hemaggulutinin HA2 of influenza virus (Schoen, P., *Gene Ther.* 6: 823-832 (1999)); Sendai virus envelope glycoproteins (Mizuguchi, H., *Biochem. Biophys. Res. Commun.* 218: 402-407 (1996)); vesicular stomatitis virus envelope glycoproteins (VSV-G) glycoprotein (Abe, A. et al., *J. Virol.* 72: 6159-63 (1998)); peptide segments or mimics of fusion enhancing proteins; and synthetic fusion enhancing peptides (e.g., Kono, K. et al., *Biochim. Biophys. Acta.* 1164: 81-90 (1993); Pecheur, E. I., *Biochemistry* 37: 2361-71 (1998); and U.S. Pat. No. 6,372,720).

Liposomes also include vesicles derivatized with a hydrophilic polymer, as provided in U.S. Pat. Nos. 5,013,556 and 5,395,619, hereby incorporated by reference, (see also, Kono, K. et al., *J. Controlled Release* 68: 225-35 (2000); Zalipsky, S. et al., *Bioconjug. Chem.* 6: 705-708 (1995)) to extend the circulation lifetime in vivo. Hydrophilic polymers for coating or derivation of the liposomes include polyethylene glycol, polyvinylpyrrolidone, polyvinylmethyl ether, polyaspartamide, hydroxymethyl cellulose, hydroxyethyl cellulose, and the like. In addition, as described above, attaching proteins that bind a cell surface protein which is endocytosed, e.g., capsid proteins or fragments thereof tropic for a particular cell types and antibodies for cell surface proteins which undergo internalization (see Wu et al, supra; Wagner et al., supra), may be used for targeting and/or facilitating uptake of the liposomes to specific cells or tissues.

Liposomes are prepared by ways well known in the art (see, e.g., Szoka, F. et al., *Ann. Rev. Biophys. Bioeng.* 9: 467-508 (1980)). One typical method is the lipid film hydration technique in which lipid components are mixed in an organic solvent followed by evaporation of the solvent to generate a lipid film. Hydration of the film in aqueous buffer solution, preferably containing the subject compounds and compositions, results in an emulsion, which is sonicated or extruded to reduce the size and polydispersity. Other methods include reverse-phase evaporation (see, e.g., Pidgeon, C. et al., *Biochemistry* 26: 17-29 (1987); Duzgunes, N. et al., *Biochim. Biophys. Acta.* 732: 289-99 (1983)), freezing and thawing of phospholipid mixtures, and ether infusion.

In another preferred embodiment, the carriers are in the form of microparticles, microcapsules, microspheres and nanoparticles, which may be biodegradable or non-biodegradable (see, e.g., *Microencapsulates: Methods and Industrial Applications, Drugs and Pharmaceutical Sciences*, Vol 73, Benita, S. ed, Marcel Dekker Inc., New York, (1996); incorporated herein by reference). As used herein, microparticles, microspheres, microcapsules and nanoparticles mean a particle, which is typically a solid, containing the substance to be delivered. The substance is within the core of the particle or attached to the particle's polymer network. Generally, the difference between microparticles (or microcapsules or microspheres) and nanoparticles is one of size. Typically, microparticles have a particle size range of about 1 to about >1000 microns. Nanoparticles have a particle size range of about 10 to about 1000 nm.

A variety of materials are useful for making microparticles containing the inhibitor compound. Non-biodegradable microcapsules and microparticles include, but not limited to, those made of polysulfones, poly(acrylonitrile-co-vinyl chloride), ethylene-vinyl acetate, hydroxyethylmethacrylate-methyl-methacrylate copolymers. These are useful for implantation purposes where the encapsulated compound diffuses out from the capsules. In another aspect, the microcapsules and microparticles are based on biodegradable polymers, preferably those that display low toxicity and are well tolerated by the immune system. These include protein based microcapsulates and microparticles made from fibrin, casein, serum albumin, collagen, gelatin, lecithin, chitosan, alginate or poly-amino acids such as poly-lysine. Biodegradable synthetic polymers for encapsulating may comprise polymers such as polylactide (PLA), polyglycolide (PGA), poly(lactide-co-glycolide) (PLGA), poly(caprolactone), polydioxanone trimethylene carbonate, polyhybroxyalkonates (e.g., poly(b-hydroxybutyrate)), poly(g-ethyl glutamate), poly (DTH iminocarbony (bisphenol A iminocarbonate), poly (ortho ester), and polycyanoacrylate. Various methods for making microparticles containing the subject compounds are well known in the art, including solvent removal process (see for example, U.S. Pat. No. 4,389,330); emulsification and evaporation (Maysinger, D. et al., *Exp. Neuro.* 141: 47-56 (1996); Jeffrey, H. et al., *Pharm. Res.* 10: 362-68 (1993)), spray drying, and extrusion methods.

Another type of carrier is nanoparticles. Submicron and nanoparticles are generally made from amphiphilic diblock, triblock, or multiblock copolymers, as is known in the art. Polymers useful in forming nanoparticles include, but are limited to, poly(lactic acid) (PLA; Zambaux et al., *J. Control Release* 60: 179-188 (1999)), poly(lactide-co-glycolide), blends of poly(lactide-co-glycolide) and polycarprolactone, diblock polymer poly(1-leucine-block-1-glutamate), diblock and triblock poly(lactic acid) (PLA) and poly(ethylene oxide) (PEO) (De Jaeghere, F. et al., *Pharm. Dev. Technol.* 5: 473-83 (2000)), acrylates, arylamides, polystyrene, and the like. As described for microparticles, nanoparticles may be non-biodegradable or biodegradeable. In addition, nanoparticles may be made from poly(alkylcyanoacrylate), for example poly (butylcyanoacrylate), in which the compound to be delivered is absorbed onto the nanoparticles and coated with surfactants (e.g., polysorbate 80). Methods for making nanoparticles are similar to those for making microparticles and include, by way of example and not limitation, emulsion polymerization in continuous aqueous phase, emulsification-evaporation, solvent displacement, and emulsification-diffusion techniques (see, e.g., Kreuter, J., *Nano-particle Preparation and Applications*, In Microcapsules and nanoparticles in medicine and pharmacy, M. Donbrow, ed., pg. 125-148, CRC Press, Boca Rotan, Fla., 1991; incorporated herein by reference).

Hydrogels are also useful in delivering the subject agents into a host. Generally, hydrogels are crosslinked, hydrophilic polymer networks permeable to a wide variety of drug compounds. Hydrogels have the advantage of selective trigger of polymer swelling, which results in controlled release of the entrapped drug compound. Depending on the composition of the polymer network, swelling and subsequent release may be triggered by a variety of stimuli, including pH, ionic strength, thermal, electrical, ultrasound, and enzyme activities. Non-limiting examples of polymers useful in hydrogel compositions include, among others, those formed from polymers of poly(lactide-co-glycolide), poly(N-isopropylacrylamide); poly(methacrylic acid-g-polyethylene glycol); polyacrylic acid and poly(oxypropylene-co-oxyethylene) glycol; and natural compounds such as chrondroitan sulfate, chitosan, gelatin, or mixtures of synthetic and natural polymers, for example chitosan-poly(ethylene oxide). The polymers are crosslinked reversibly or irreversibly to form gels embedded with the inhibitor compound, or pharmaceutical compositions thereof (see, e.g., U.S. Pat. Nos. 6,451,346; 6,410,645;

6,432,440; 6,395,299; 6,361,797; 6,333,194; 6,297,337 Johnson, O. et al., *Nature Med.* 2: 795 (1996); incorporated by reference in their entirety).

Another pharmaceutical compositions may include those in the form of transdermal patches for delivery of the compounds through the skin by diffusion or electrically mediated transport (see, e.g., Banga, A. K. et al., *Int J Pharm.* 179(1): 1-19 (1999); U.S. Pat. Nos. 5,460,821, 5,645,854, 5,853,751, 6,635,274, 6,564,093; all publications incorporated herein by reference.).

In some embodiments, the inhibitors may be provided as a depot, such as a slow release composition comprising particles, a polymer matrix (e.g., a collagen matrix, carbomer, etc.) that maintains release of compounds over an extended period of time, use of a pump which continuously infuses the inhibitor compounds over an extended period of time with a substantially continuous rate, and the like. These and other combinations of administering effective dosages will be apparent to those skilled in the art.

The inhibitor compounds may be provided in the form of a kit or packaged formulation. A kit or packaged formulation as used herein includes one or more dosages of an HMG CoA reductase inhibitor, or salts, solvates or hydrates thereof in a container holding the dosages together with instructions for administration to a host. For example, the package may contain the HMG CoA reductase inhibitors along with a pharmaceutical carrier combined in the form of a powder for mixing in an aqueous solution, which can be ingested by the afflicted subject. Another example of packaged drug is a preloaded pressure syringe, so that the compositions may be delivered intravenously, intramuscularly. The package or kit includes appropriate instructions, which encompasses diagrams, recordings (e.g., audio, video, compact disc), and computer programs providing directions for use of the combination therapy.

6.3 Methods of Measuring Cognitive Function

To determine whether a subject is afflicted with a cognitive deficit and/or to determine improvement or restoration of cognitive function, a variety of tests may be employed for both animal model systems and for assessing individual patients. These include tests ranging from assessments of general cognitive ability to measurement of specific physiological processes associated with cognitive function.

The global examination of cognitive deficits may employ those commonly used for diagnosing such disorders as described in various reference works, such as *Diagnostic and Statistical Manual of Mental Disorders*, 4$^{th}$ Ed., American Psychiatric Association; (2000) (acronym DSM) and the International Classification of Disease (ICD), 10$^{th}$ Revision, World Health Organization (WHO) (2003). The DSM provides a basis for selecting the disorder from a classification that best reflects the signs and symptoms displayed by the individual being evaluated (diagnostic classification); a set of diagnostic criteria that indicates what symptoms must be present (and for how long) in order to qualify for a diagnosis (i.e., inclusion criteria) as well as those symptoms that must not be present (i.e., exclusion criteria) in order for an individual to qualify for a particular diagnosis (diagnostic criteria sets); and a description of each disorder that includes diagnostic features, subtypes of the disorder, culture, age, and gender features, prevalence, course of the disorder, hereditary pattern, and differential diagnosis. For instance, in an exemplary embodiment for diagnosing ADHD, the DSM indicates a diagnosis when the subject suffers from 6 or more symptoms of inattention that persists for more than 6 months that is maladaptive and inconsistent with the developmental level, and/or 6 or more symptoms of hyperactivity-impulsivity that has persisted for more than 6 months that is maladaptive or inconsistent with the developmental level.

The ICD is a more general reference work for all diseases and includes classifications diseases and other health problems recorded on many types of health and vital records, including death certificates and hospital records. ICD provides descriptions of mental and behavioral disorders (Chapter V); diseases of the nervous system (Chapter IV); congenital malformations, and chromosomal abnormalities (Chapter XVII). The DSM and ICD systems provide a set of standard criteria for effectively and reliably diagnosing a broad range of cognitive disorders.

Exemplary tests for cognitive function may use any number of procedures used in the art. In some embodiments, the analysis of cognitive function may use that described in Roid, G., *Stanford-Binet Intelligence Scale,* 5th Ed., Riverside Publishing, which is a standardized test that assesses intelligence and cognitive abilities in children and adults, generally of ages of about 2-85+ years. The test measures four areas that include verbal reasoning, quantitative reasoning, visual-spatial processing, and working memory. These areas are covered by subtests for measuring vocabulary, comprehension, verbal absurdities, pattern analysis, matrices, paper folding and cutting, copying, quantitative, number series, equation building, memory for sentences, memory for digits, memory for objects, and bead memory. The tests identify a distinct hierarchy of abilities from normal to affected patients.

In some embodiments, the test for cognitive function may use the Mini-Mental State Exam (MMSE) and variations thereof (Folstein, M. F. et al., *J. Psych. Res.* 12:189-198 (1975)). MMSE is a test of cognitive status that typically takes between 5 and 10 minutes to administer. Areas measured on the MMSE include orientation to time and place, immediate and delayed verbal recall memory, attention, concentration, naming, repetition, following a 3-step command, following a written command, sentence writing, and visual-motor copying. Performance on each of the tasks is numerically graded with a maximum score of 30, with scores lower than 23 being considered indicative of cognitive impairment. The MMSE may be used to identify patients with cognitive disturbance from those without such disturbance and is also applicable to measuring the changes in cognitive state upon treatment. This test as well as others described herein and known in the art may be used in combination with other tests to substantiate or correlate the results.

In other embodiments, the test for cognitive function is the Wechsler Intelligence Scale for Children or Adults. The test for adults has two sections, a verbal and a performance measurement. The verbal section has a general knowledge test, a digit span test in which subjects are given sets of digits to repeat initially forwards then backwards (auditory recall and short term memory), a vocabulary test to measure expressive word knowledge, an arithmetic tests that measures distractibility as well as numerical reasoning, a comprehension test that focuses on issues of social awareness, and a similarities test for measuring concept formation that asks subjects to specify how two seemingly dissimilar items might in fact be similar. The performance section involves picture completion test (small pictures that all have one vital detail missing) that measures attention to detail, picture arrangement test where the subject is required to arrange them into a logical sequence, a block design test that involves putting sets of blocks together to match pattern on cards, digit symbol test that involves copying a coding pattern, and object assembly test that involves solving jig-saw type puzzles. The scores on both sections are processed to arrive at a numerical intelligence quotient (IQ).

The Wechsler Intelligence Scale for Children is similar to the adult test, having a verbal section and a performance section. The verbal sections involve general knowledge test (oral, general information questions), a similarities test that requires explaining how two different things or concepts are similar, an arithmetic test that uses verbally framed math applications problems without paper, a vocabulary test that requires giving oral definitions of words, a comprehension test that measures social and practical understanding, and a digit span test that requires repeating dictated series of digits forwards and backwards. The performance section involves a picture completion test (identifying missing parts of pictures, coding A test (marking rows of shapes with different lines according to a code as quickly as possible), coding B test (transcribing a digit-symbol code as quickly as possible), a picture arrangement test (sequencing cartoon pictures to make sensible stories), a block design test (copying small geometric designs with four or nine larger plastic cubes), an object assembly test (puzzles of cut-apart silhouette objects with no outline pieces), symbol search test (deciding if target symbols appear in a row of symbols), and maze tests (no pencil lifting, points off for entering blind alleys). As with the adult version, full scale IQ is based on the tests in the verbal and performance scales.

Other embodiments for measuring cognitive function include, among others, Test of Nonverbal Intelligence and Comprehensive Test of Nonverbal Intelligence. Related tests may be used to assess specific brain areas as they relate to attention, executive function, language, memory and visual-spatial and visual-motor skills. Non-limiting examples of these types of tests include NEPSY: A Development Neuropsychological Assessment; Delis-Kaplan Executive Function System (D-KEFS); Comprehensive Test of Phonological Processing (CTOPP); Rey-Osterrieth Complex Figure Test; Children's Memory Scale, Wechsler Memory Scale—Third Edition (WMS-III); Woodcock-Johnson (WJIII) Tests of Cognitive Abilities; Beery-Buktenica Developmental Test of Visual Motor Integration; Wisconsin Card Sorting Test (WCST); Children's Category Test, Judgment of Line Orientation; Behavior Rating Inventory of Executive Function; and Wide Range Assessment of Memory and Learning (WRAML).

Some tests of cognitive function have been developed that are useful extrapolations to animal model systems. Many of these tests are based on operant and non-operant problem solving tasks. General tests include delayed matching sample to sample (short term memory), repeated acquisition (learning), temporal discrimination (timing ability), condition and position response, and progressive ratio (see Slikker et al., *Toxicological Sciences* 58:222-234 (2000)).

In some embodiments, the test for cognitive function in some animal model systems is a water maze test, generally known as the Morris water maze test, typically used to test learning and memory in small animals such as rats and mice. The Morris water maze consists of a round tank (pool) of water with a submerged hidden escape platform from the water. Extra-maze cues, to test spatial learning, may be placed around the tank at positions visible to the test animal. The ability of the test animal to find the submerged platform provides a measure of the learning and memory function. Malperformance in the Morris water maze test has been associated with impaired LTP.

In other embodiments, the cognitive test is a fear conditioning test, which allows for the assessment of learning and memory of aversive events. Fear conditioning typically relies on the ability of normal animals to learn to fear a previously neutral stimulus because of its temporal association with an aversive stimulus, such as an electric shock, noxious odor, or a startling noise. Typically, the test animal is placed in a conditioning chamber (context) before the onset of a discrete stimulus (the conditioned stimulus or CS), such as a discrete tone. The tone is followed by the aversive stimulus, such as an electrical shock to the foot. The task allows for the simultaneous assessment of learning about simple, unimodal cues and learning about complex, multimodal stimuli such as context. A related test is the startle test, which is used to measure a number of behaviors, including basic startle, pre-pulse inhibition, and fear potentiation of the startle response.

Another type of cognitive test for experimental systems is the Radial Arm Maze. An exemplary maze of this type has a number of arms (e.g., 8) that extend outward from a circular central arena. One or more of the arms is baited to contain a reward and the animal tested for their ability to consume the bait as a function of time. This cognitive test is used to measure spatial learning and memory. Some versions of the task can be used to examine both working and reference memory, such as by measuring the number of reference memory errors (entering an arm that does not contain the reward) and working memory errors (entering an arm containing the reward but previously entered). Like the water maze, this task is sensitive to hippocampal function.

In other embodiments, the cognitive test is a social recognition test that is used to measure social learning and memory. Animals are tested for their ability to remember conspecifics over various time intervals. This may test a variety of cognitive tasks, such as the ability to learn about the safety of food from its conspecifics by sampling those food odors on the breath of littermates. This test may also provide information on aggression and social interaction with non-littermate conspecifics. Memory components can be assessed by repeated exposures to the different stimulus at various frequencies.

In further embodiments, the cognitive test may be an open field test, which evaluates the subject for hyperactivity, exploratory activity, and stereotyped rotation in a test chamber. Additional behavior in this type of test includes, among others, time taken to move to the edges of the open field apparatus, total activity in the open field, and percentage of time spent in the periphery. Versions of the task are used to assess anxiety and memory for context.

In yet other embodiments, the cognitive test is the SHIRPA Primary Screen, as described in Rogers, D. C. et al., *Mamm. Genome* 8:711-713 (1997)). This test examines the behavioral and functional profile of the animal by an initial evaluation of the undisturbed behavior in a testing chamber and then under a series of manipulations to elicit a behavioral response from the animal. In the test, observations are made of gait or posture, motor control and co-ordination, changes in excitability and aggression, salivation, lacrimation, piloerection, defecation and muscle tone. In addition to these scored behaviors, the animal is evaluated for other types of stereotyped behavior including, convulsions, compulsive licking, self-destructive biting, retropulsion and indications of spatial disorientation. Initial observations are followed by a sequence of manipulations using tail suspension and the grid across the width of the arena. To complete the assessment, the animal is restrained in a supine position to record autonomic behaviors prior to measurement of the righting reflex. Throughout this procedure vocalization, urination and general fear, irritability or aggression are recorded.

Where a biochemical or molecular defect, such as a genetic abnormality is suspected, the cognitive tests may be used in conjunction with tests used to determined existence of the biochemical or genetic abnormality. Tests include analysis for gross chromosomal abnormalities (e.g., metaphase chromosome), and techniques for determining specific genetic defects, which include as non-limiting examples, polymerase chain reaction, nucleic acid sequencing, nucleic acid hybridization, restriction fragment length analysis (for RFLP), single stranded conformational polymorphism, and fluorescence in situ hybridization (FISH). For example, defects in NF-1 gene may be based on RFLP (Jorde, L. B. et al., *Am J Hum Genet.* 53(5):1038-50 (1993)); polymerase chain reaction (Abernathy, C. et al., *Clin Genet.* 45(6):313 (1994)); and single stranded conformational polymorphism (Gomez, L., *Cancer Genet Cytogenet.* 81(2):173-4 (1995)). Corresponding physiological (facial and limb features) and developmental characteristics may also be assessed to supplement the diagnosis.

In some embodiments, the test for the cognitive defect is an in vitro test that measures molecular correlates of the processes thought to be involved in cognitive function. In some embodiments, the test is an electrophysiology test for LTP (see, e.g., Bliss and Collingridge, *Nature* 361: 31-39 (1993)). In its basic format, slices of the hippocampus containing the CA1 region, or other suitable neural systems, are removed and a train of stimuli used to evoke action potentials in presynaptic neurons. With certain types of presynaptic stimulation, enhancement of the excitatory postsynaptic potentials (EPSPs) is observed that can last for day or weeks. Induction of LTP is dependent on $Ca^{2+}$ entry into the postsynaptic neuron triggered by N-methyl-D-aspartate receptor activation (see, e.g., Tsien, R. et al. *Cell* 87:1327-1338 (1996)). As discussed above, LTP may be generated in hippocampal cultures by stimulation of a single input pathway (i.e., homosynaptic) by a train of evoked potentials. Early phase or E-LTP may be induced by a single high-frequency tetanic stimuli while late phase or L-LTP is typically induced by multiples of such tetanic trains (see, e.g., Thomas, M. J. et al., *J Neurosci.* 18:7118-7126 (1998)). L-LTP may also be induced by paired stimulation of multiple input pathways (i.e., heterosynaptic), where activation of one afferent pathway is paired to a conditioning stimulus in another afferent pathway in the neural network (Huang, Y. Y. et al., *Proc. Natl. Acad. Sci. USA* 101(3):861-864 (2004)).

To determine whether the LTP is the early phase or the longer lasting phase, various pharmacological agents may be added to the cultures. These include as non-limiting examples, transcription inhibitors, protein synthesis inhibitors, and inhibitors of enzymes thought to be critical for establishment of LTP. Transcription inhibitors include, among others, alpha amanitin, actinomycin D, cordycepin, and 5,6-dichloro-1-D-ribofuranosylbenzimidazole. Protein synthesis inhibitors useful in these in vitro tests include anisomycin, cycloheximide, emetine, rapamycin (Cammalleri, M. et al., *Proc Natl Acad Sci USA* 100(24):14368-73 (2003)), and puromycin, Enzyme inhibitors may include enzymes involved in formation of LTP, including protein kinase A inhibitors (e.g., KT5720), protein kinase C inhibitors (e.g., chelerythrine); tyrosine kinase inhibitors (e.g., genistein); calmodulin kinase (CaMK) inhibitors (e.g., autocamtide-2-related inhibitory peptide (AIP) (KKALRRQEAVDAL). These compounds may be used in combination with the HMG CoA reductase inhibitors (or other modulators of the isoprenoid pathway) to determine the effect of inhibitors on LTP.

It is to be understood that other types of tests known in the art may be used for the purposes described above, and are to be included within the scope of the methods described herein.

7. EXAMPLES

7.1 Example 1

Treatment of Learning Deficits in an Animal Model of Neurofibromatosis-1

7.1.1 Animal Experiments

All animal protocols were approved by the Chancellor's Animal Research Committee at the University of California at Los Angeles, in accordance with the National Institutes of Health guidelines. All the animals were 129T2/SvEmsJ-C57BL/6N F1 hybrids generated by an F1 cross between nf1+/− mice (maintained in the C57BL/6N background for more than 11 generations) and wild-type mice on the 129T2/SvEmsJ background. In every experiment, the controls were the littermates of the mutants. All experiments were carried out blind with respect to genotype and treatment.

7.1.2 Western Blot Analysis for p44/42 MAP Kinase Phosphorylation and p21Ras Activity Hippocampus from control and lovastatin-treated mice were isolated and homogenized in protein extraction buffer, with 1% Triton X-100, 25 mM HEPES pH 7.5, 150 mM NaCl, 10% Glycerol, 2 mM EDTA, 1 ug ml-1 leupeptin (Sigma), 100 ug ml-1 PMSF (Sigma), 10 mM NaF (Sigma), 25 mM Na glycerophosphate (Sigma) and 1 mM $Na_3VO_4$ (Sigma). Supernatant was collected after 10 min of 13,000 rpm centrifugation. Protein concentrations were determined by bicirchoninic acid protein assay (Pierce). Lysates were added to SDS loading buffer and boiled 2 min. Products were separated by electrophoresis on a 4-15% SDS-PAGE gradient gel (Bio-Rad Laboratories Inc.). Gels were blotted to Nitrocellulose membranes (Bio-Rad) at 15 V in 25 mM Tris, 192 mM glycine and 20% (v/v) methanol, then blocked for 1 h at room temperature with Tris-buffered saline (TBS) containing 0.1% (v/v) Tween-20 and 5% (w/v) non-fat dry milk. After washing in TBST, membranes were hybridized 1 h at room temperature with anti-phospho-p44/42 (Cell Signaling) antibody diluted 1:1,000 in TBS, 0.1% (v/v) Tween 20 and 5% (w/v) non-fat dry milk. The membranes were then processed by ECL Plus protocol (Amersham BioSciences, Inc.) for visualization of the bands. Membranes were stripped in Strip buffer (Pierce) for 15 min at room temperature, then probed with anti-p44/42 (cell Signaling) as a control to normalize equal protein loading. Phosphorylated p44/42 and p44/42 migrated at a relative molecular mass of 42,000 44,000.

7.1.3 p21Ras Activity Assay

For p21Ras activity assay, p21Ras pull-down experiments were performed with the EZ-detect p21Ras activation kit (Pierce Biotechnology) according to the manufacturer's protocol. Hippocampal lysates (200 mg) from different groups were incubated with 40 mg GST-Raf1-RBD and one Swell Gel Immobilized Glutathione Discs at 4oC. for 2 h. The resin was washed 4 times with Lysis/Binding/Wash buffer and 50 ul of 2×SDS Sample buffer (125 mM Tris-HCl, pH 6.8, 2% glycerol, 4% SDS, 0.05% bromophenol blue, and 5% 2-mercaptoethanol) was added. The spin columns were centrifuged at 7,200×g for 2 min and the collected solution was boiled for 5 min. Samples were applied 25 ml per lane on SDS-PAGE. p21Ras was detected by Western blotting as described using an anti-pan-p21Ras antibody (Sigma).

7.1.4 Hippocampal LTP

Transverse hippocampal slices (400 mm thick) were place in a submerged recording chamber perfused (2 ml/min) with artificial cerebrospinal fluid containing 120 mM NaCl, 3.5 mM KCL, 2.5 mM $CaCl_2$, 1.3 mM $MgSO_4$, 1.25 mM $NaH_2PO_4$, 26 mM $NaHCO_3$ and 10 mM D-glucose at 34° C.

Extracellular excitatory postsynaptic field potentials (EPSPs) were recorded with a Pt/Ir electrode (FHC, Bowdoinham, Me.) from the stratum radiatum layer of the area CA1, and the Schaffer collateral/commissural afferents were stimulated with two bipolar electrodes placed one on either side of the recording electrode (300 microns from the recording electrode). Test pulses were alternated each minute between the two electrodes throughout the duration of the experiment. The stimulation intensity used during the experiment was 60 mA. After the responses were monitored at least for 20 min to ensure a stable baseline, LTP was induced with a single tetanus delivered to one pathway (the test pathway) using a five-theta burst stimulation (TBS) protocol (five bursts, each burst 4 pulses at 100 Hz, 200 ms inter-burst interval). The untetanized pathway served as a control pathway. Slices in which there was significant drift in the control pathway were excluded from further analysis. When multiple slices were used from a single animal, data were averaged and then entered into analysis as a single subject. Thus, all data reported reflect individual mice rather than individual slices. To determine whether the magnitude of LTP differed significantly between the groups, responses from the last 10 min block of recordings (40-50 min) were compared. Mice were injected with 10 mg/kg of lovastatin subcutaneously once per day for 4 days and sacrificed on the 4th day, 6 hours following the final injection. Slices were then prepared as described above.

7.1.5 Water Maze Test

The basic protocol for the water maze experiments has been previously described. Mice from the 129T2/SvEmsJ-C57B/6N F1 genetic background were given two trials per day (30-s inter-trial intervals) with a probe trial (60 s) at the end of training day 5 and 7. Mice were given subcutaneous injections of 10 mg/kg lovastatin or vehicle for 3 days before the 1st training day and then 6 hours before training every day.

7.1.6 Lovastatin Solution and Pellet

Because of the extended nature of the lateralized reaction time task (see below), lovastatin was administered orally as pellets. 100 mg mevinolin (lovastatin, Sigma Inc.) in the lactone form was dissolved in 2 ml of warm (55° C.) ethanol, then 0.6 ml 1N NaOH and 20 ml water were added. The solution was incubated at room temperature for about 30 min to complete the conversion of mevinolin to the sodium salt. The final mevinolin solution (4 mg/ml) was adjusted to pH7.5 with HCl and the volume was brought to 25 ml 10. Vehicle was prepared in the same way except that mevinolin was omitted. Lovastatin tablets (Eon Labs) (prescription formulation) were crushed into powder and mixed with melted peanut butter chips (H.B. Reese Candy Co.) and molded to 200 mg pellet. Each pellet contained 0.15 mg Lovastatin. The pellet was administered orally (10 mg kg−1 dose) to mice once daily.

7.1.7 Lateralized Reaction Time Task

Mice (Placebo-treated: nf1+/−=14, WT=10; lovastatin treated: nf1+/−=7, WT=7) subjects were initially deprived of food to 90% of their free-feeding weights. Mice were fed 1.5 gm of chow every day in their home cages (1 hr after experiment). Lovastatin animals received 1.1 gm of chow plus 400 mg pellets contain 0.3 mg lovastatin (10 mg/kg) every day. Mice were trained in miniaturized versions of a "5-choice" box (Med Associates Inc., St Albans Vt.) that was equipped with a curved wall with horizontal array five apertures that could be internally illuminated. The opposite wall was fitted with a food receptacle where pellets were delivered as reinforcers. The animals were shaped to produce a "poke and hold" response in the central aperture. A correct response was scored when the animals correctly poked a side aperture that had been indicated during the poke and hold response. The side apertures were initially illuminated for 30 seconds, which was gradually decreased to 1 second over a period of weeks. When animals performed at 75% accuracy at 1 second target stimulus duration they entered the test phase. Mice were tested on a variable duration condition in which the target aperture was illuminated for 0.5, 1.0 or 2.0 sec (varied from trial to trial within the session). Correct responses/total trials were measured, which vary as a function of the target stimulus duration and was therefore analyzed with repeated measures analysis of variance (the repeated measure being stimulus duration).

7.1.8 Prepulse Inhibition

Mice subjects were initially deprived of food to 90% of their free-feeding weights and subsequently fed 1.5 gm of chow or 1.1 gm of chow plus 400 mg of pellets containing 0.3 mg lovastatin (10 mg/kg) every day in their home cages for 3 months. Following an acclimation period of 5 min, mice were presented with a total of 20 noise bursts (40 ms duration, 120 dB, <1 ms rise/fall time). In the prepulse inhibition phase, mice were presented with a total of 90 trials. Three prepulse intensities were tested: 70, 75 and 80 dB. Prepulses were 20 ms in duration with a rise/fall time of less than 1 ms. For each prepulse intensity, there were three types of trial: prepulse alone, prepulse/startle stimulus and startle stimulus alone. In the prepulse/startle stimulus trial, the onset of the prepulse preceded the onset of the startle stimulus by 100 ms. Background noise levels were maintained at 68 dB throughout testing, and the trials were spaced 15 s34.

7.1.9 Statistical Analysis

Data acquired from the water maze were analyzed by repeated-measures ANOVA. Percent time in training quadrant for the different genotypes was analyzed using 2-way ANOVA. Planned comparisons using a paired t-test were used to analyze the proximity data. Attention data was analyzed using three-way repeated-measures ANOVA on the average of correct response rate. PPI data was analyzed using two-way repeated-measures ANOVA. For the electrophysiological experiments, the significance of differences between the groups was determined by two-way ANOVA. Post-hoc comparisons (Fisher's PLSD) between groups were carried out where appropriate.

7.1.10 Results of Lovastatin Treatment

Lovastatin, a specific inhibitor of the rate-limiting enzyme in cholesterol biosynthesis (HMG-CoA reductase), is widely used to treat hyperlipidemia in humans. Interestingly, previous studies have shown that lovastatin can inhibit p21Ras isoprenylation and activity. Since the cognitive deficits caused by mutations in the NF1 gene may result from increased p21Ras activity, studies were conducted to determine whether lovastatin could rescue these deficits. Pharmacokinetic data in mice indicate that the dose used for most of the mouse experiments described here (10 mg kg−1) results in total plasma drug levels similar to those normally present in patients taking lovastatin (data distributed by Merck & CO., Inc; available at world wide web (www) druginfonet.com/mevacor.htm). The biochemical studies show that this dose was effective at ameliorating the abnormally high p21Ras/MAPK activity in nf1+/− mice (FIG. 1).

The effect of lovastatin treatment on p21Ras/MAPK was determined using western blotting. Mice were injected with 0-50 mg/kg lovastatin subcutaneously once per day for 4 days, and sacrificed on the 4th day, 6 hours after the final injection. Hippocampal extracts were prepared; proteins were resolved by SDS-PAGE and transferred to membranes, hybridized with anti-phospho p44/42 MAPK (Cell Signaling) antibody and visualized with ECL-Plus (Amersham Biosciences). The results showed that lovastatin decreased the amount of phosphorylated p44/42 MAPK (the active form) in a dose-dependent fashion (FIG. 1a). The results in FIG. 1b demonstrate that 10 mg/kg of lovastatin, the dose used in the electrophysiological and behavioral experiments described below, decreased the levels of phosphorylated p44/42 MAPK in nf1+/− mice. Additionally, the results also showed that the levels of phosphorylated p44/42 MAPK in nf1+/− mice are higher than in wild-type littermates (WT). The nitrocellulose membranes used for the analysis just described were also re-probed with an anti-p44/42 MAPK antibody to control for sample loading.

Neurofibromin functions as a p21Ras GTPase activating protein which catalyzes the conversion of active GTP-bound p21Ras to the inactive GDP-bound form. The impact of lovastatin treatment on p21Ras activity was assessed directly. Hippocampal extracts were reacted with GST-Raf1-RBD beads (Pierce Bio), which specifically bind p21Ras-GTP, the active form of p21Ras. p21Ras-GTP was resolved by SDS-PAGE and visualized with an anti-pan p21Ras antibody (Sigma). The results showed that lovastatin decreased the hippocampal levels of p21Ras-GTP in WT (FIG. 1c), just as it decreased the levels of MAPK activity, and that these levels were higher in nf1+/− mice. Altogether these data demonstrate that lovastatin can decrease p21Ras/MAPK activity in the hippocampus and may therefore be useful to treat the hippocampal LTP and cognitive deficits of the nf1+/− mice.

A previous study had shown that the learning deficits of the nf1+/− mice are likely caused by impairments in LTP, a stable long-lasting change in synaptic strength widely believed to be a key cellular mechanism for learning and memory. Therefore, experiments were conducted to determine whether the LTP deficits in nf1+/− mice could be reversed by lovastatin. Mice were injected with 10 mg/kg of lovastatin subcutaneously once per day for 4 days and sacrificed on the 4th day, 6 hours following the final injection. LTP in hippocampal slices at the Schaffer collateral/CA1 synapse were examined since LTP at this synapse has been implicated in hippocampal learning and memory. LTP was measured after a five theta-burst stimulation protocol (TBS, five bursts 200 ms apart, each burst of 4 pulses at 100 Hz), which mimics in vivo activity of hippocampal neurons during exploratory behavior. FIG. 2 shows that there was a difference among the genotypes and treatments (ANOVA, F1, 26=8.55, P<0.05). The LTP measured in nf1+/− mutants was significantly lower than in WT mice (PLSD, P<0.05; FIG. 2), a result consistent with previously published findings. The amount of LTP induced in nf1+/− mutants treated with lovastatin was significantly higher than that induced in mutants (PLSD, P<0.05; FIG. 2), and equivalent to that of WTs (PLSD, P=0.602; FIG. 2). These data demonstrate that the lovastatin treatment completely reversed the LTP deficits of the nf1+/− mice. Thus, treated animals were further examined to determine whether statins could reverse the cognitive deficits associated with NF− in mice.

Spatial problems are among the most common cognitive deficits in individuals affected with NF1. It was previously shown that nf1+/− mice have abnormal spatial learning tested in the hidden version of the water maze, a task that is sensitive to hippocampal lesions. To test the hypothesis that lovastatin can rescue the deficits of nf1+/− mice in this hippocampal-dependent task, just as it rescued their hippocampal p21Ras/MAPK and LTP abnormalities, animals were injected with 10 mg/kg lovastatin subcutaneously for 3 days before the 1st training day, and then 6 hours before behavioral training daily. Mice were trained with two trials per day. No differences were observed between genotypes and/or treatment groups in measures of acquisition, floating, thigmotaxic behaviour or swimming speed (data not shown), confirming that just as in humans nf1 mutations in mice cause selective deficits in cognitive function.

Spatial learning was assessed in probe trials given at the end of water maze training on days 5 and 7 since previous studies showed that probe trial performance is the most faithful measure of spatial learning in the Morris maze. In the probe trials the platform was removed from the pool and the mice were allowed to search for it for 60 seconds. There was no significant difference between WT and nf1+/− mice in the day 5 probe trial, because at this time neither group showed clear evidence of having learned the task (FIG. 3a). After two more days of training, it was observed that the time spent searching in the training quadrant during the day 7 probe trial was different among the different genotypes and treatments (ANOVA, F1,82=4.415, P<0.05). WT mice spent significantly more time searching in the training quadrant than nf1+/− mice (PLSD, P<0.05; FIG. 3b), confirming that the nf1+/− mutants have impaired spatial learning. In contrast, the mutants treated with lovastatin spent as much time as WTs in the training quadrant (P=0.862; FIG. 3b), and significantly more time than mutants given placebo (P<0.05).

The lovastatin-mediated rescue of the spatial learning deficits in nf1+/− mice was confirmed using another measure of learning during the probe trial (proximity). All groups, except nf1+/− mice on placebo (t21=0.313; P=0.757), searched closer to the exact platform position than to the opposite position in the pool (WT paired t-test, t22=6.274, P<0.0001; WT on lovastatin t19=2.159, P<0.05; nf1+/− mice on lovastatin t20=2.170, P<0.05; FIG. 3c). These results demonstrate that the spatial learning deficits of the nf1+/− mice are not caused by irreversible developmental abnormalities since they are reversed with acute lovastatin treatment in adult mutant mice.

Besides spatial impairments, NF-1 patients also show attention deficits. Thus, it was investigated whether nf1+/− mice also exhibit impairments in attention, and whether lovastatin could rescue those deficits. For this purpose, a lateralized reaction-time task, a test that measures divided visuospatial attention, was used. In this task, animals produce a fixation response that triggers the delivery of a variable duration visual target stimulus in one of their visual fields; the spatial location and time of onset of the target is unpredictable. This task therefore requires sustained (over time) and divided (across space) attention. WT and nf1+/− mice were tested with lovastatin (nf1$^{+/-}$=7, WT=7) or placebo (nf1+/−=14, WT=10). The rate of correct responses (an index of attention accuracy) revealed a Genotype X Treatment X Target Stimulus Duration interaction (ANOVA, F2, 70=3.200, P<0.05). At the most difficult stimulus duration (0.5 sec), the correct response rate of WT mice is significantly higher than that of nf1$^{+/-}$ mice (PLSD, P<0.05; FIG. 4a), indicating that the nf1+/− mice have impaired attention. In contrast, the correct response rate of nf1+/− mice treated with lovastatin is indistinguishable from that of WT mice at target stimulus duration of 0.5 sec (PLSD, P=0.148; FIG. 4a), and significantly higher than nf1+/− given placebo (PLSD, P<0.05). These data demonstrate that nf1+/− mice exhibit substantial attention deficits and that lovastatin treatment can reverse these deficits.

Children with attention-deficit hyperactivity disorder (ADHD) are reported to have significantly reduced pre-pulse inhibition (PPI). This task assays sensory "gating" of environmental stimuli. A powerful and sudden acoustic stimulus will elicit a whole body startle response. When the startle producing stimulus is preceded by a weak pre-stimulus (by approximately 100 milliseconds) the startle response is inhibited in normal persons and animals. Previous studies show a high incidence of ADHD in NF1 and support an association between ADHD and learning problems in these children. Thus, nf1$^{+/-}$ mice were tested for deficits in this task and whether these deficits could also be reversed by lovastatin using the same treatment regimen described for the other two behavioral experiments described above. A two-way repeated measures ANOVA revealed significant main effects of Genotype and Treatment (FIG. 4b). The nf1+/− animals have deficient PPI (F1, 30=7.42, P<0.05) and lovastatin treatment resulted in an increase in performance (F1, 30=6.61, P<0.05). Importantly, the performance of nf1+/− animals on lovastatin is indistinguishable from that of WT animals on placebo (PLSD, P=0.877), demonstrating that lovastatin can reverse the PPI deficits of these mutants.

The present results demonstrate that lovastatin treatment can reverse the biochemical, electrophysiological, and cognitive deficits observed in a mouse model of NF1, and that these deficits are not due to irreversible developmental changes. Previous studies have shown that an increase in p21Ras/MAPK activity is central to the pathophysiology associated with NF1, and our biochemical data demonstrate that lovastatin reverses the abnormally elevated p21Ras/MAPK activity in an animal model of NF1. Together with previous findings, these results indicate that the ability of lovastatin to dampen the elevated p21Ras/MAPK signaling of the nf1+/− mice rescues their deficits in a cellular mechanism of learning and memory (LTP), and that this reverses the cognitive impairments of these mutants. Importantly, the studies herein demonstrate that the dose of lovastatin that is effective in nf1+/− mice did not affect cognitive function in control mice, a result consistent with randomized studies performed with human subjects that did not identify a reliable effect of lovastatin on cognitive function. Although it is worth noting that there are sporadic reports that statins can be associated with mild cognitive impairment, this study used doses of lovastatin which, based on pharmacokinetic data, should produce a total plasma drug exposure of less than 0.3 times that of typical human doses (i.e., an 80 mg/day dose). Altogether, the studies reported here demonstrate that the cognitive deficits associated with NF-1 can be reversed by treatments with lovastatin, a widely prescribed drug that is known to be well-tolerated even in long-term treatments. Thus, these data suggest that lovastatin could be used to treat the cognitive impairments associated with NF-1 in humans.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

All patents, patent applications, publications, and references cited herein are expressly incorporated by reference to the same extent as if each individual publication or patent application was specifically and individually indicated to be incorporated by reference.

What is claimed is:

1. A method of treating a subject with a cognitive deficit, comprising: administering an effective amount of a hydroxymethylglutaryl CoA (HMG CoA) reductase inhibitor to a subject afflicted with a cognitive disorder associated with the NF-1 genetic defect, wherein the inhibitor comprises a statin.

2. The method of claim 1, wherein the statin is selected from the group consisting of atorvastatin, cerivastatin, fluvastatin, lovostatin, pravastatin, pitavastatin, rovustatin, simvastatin, and compatible mixtures thereof.

3. The method of claim 1, wherein the inhibitor comprises a mixture of HMG CoA reductase inhibitors.

4. The method of claim 1, wherein the effective amount does not significantly lower total serum cholesterol level in the subject.

5. The method of claim 1, wherein the cognitive disorder is associated with dysregulation of small monomeric GTP binding protein activity.

6. The method of claim 5, wherein the small monomeric GTP binding protein activity is that of RAS protein.

7. The method of claim 6, wherein the activity of RAS protein is associated with the NF-1 genetic defect.

8. The method of claim 1, wherein the cognitive disorder is associated with dysregulation of mitogen activated protein kinase (MAPK) signaling pathway.

9. The method of claim 1, wherein the cognitive disorder is associated with increased inhibitory neuronal activity.

10. The method of claim 9, wherein the inhibitory neuronal activity is associated with increased GABA-mediated inhibition.

11. The method of claim 10, wherein the GABA-mediated inhibition is associated with activity of $GABA_A$.

12. The method of claim 10, wherein the GABA-mediated inhibition is associated with activity of $GABA_B$.

13. The method of claim 1, further comprising administering a farnesyl transferase inhibitor to the subject.

14. The method of claim 1, further comprising administering a geranylgeranyl transferase inhibitor to the subject.

15. The method of claim 1, further comprising administering an inhibitor of γ-aminobutyric acid (GABA) mediated inhibition to the subject.

16. The method of claim 1, wherein the inhibitor comprises an inhibitor of GABA receptor activity.

17. The method of claim 15, wherein the inhibitor of GABA receptor activity is selective for $GABA_A$.

18. The method of claim 15, wherein the inhibitor of GABA receptor activity is selective for $GABA_B$.

19. The method of claim 1, wherein the administering is by adjunctive administration.

20. The method of claim 19, wherein the adjunctive administration is simultaneous administration.

21. The method of claim 19, wherein the adjunctive administration is sequential administration.

22. The method of claim 1, wherein said subject has a normal cholesterol level.

* * * * *